(12) United States Patent
Avalle-Bihan et al.

(10) Patent No.: US 10,072,266 B2
(45) Date of Patent: Sep. 11, 2018

(54) STAT5 INHIBITORS AND USE THEREOF

(71) Applicants: CENTRE NATIONAL DE LA RECHERCHE SCIENTIFIQUE (CNRS), Paris (FR); UNIVERSITE DE TECHNOLOGIE DE COMPIEGNE, Compiegne (FR)

(72) Inventors: Berangere Avalle-Bihan, Compiegne (FR); Claire Loussouarn, Le Meux (FR); Hassan Isber, Compiegne (FR); Alain Friboulet, Jonquieres (FR); Severine Padiolleau, Morienval (FR)

(73) Assignees: UNIVERSITÉ DE TECHNOLOGIE DE COMPIÈGNE, Compiègne (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/127,535

(22) PCT Filed: Mar. 20, 2015

(86) PCT No.: PCT/FR2015/050711
§ 371 (c)(1),
(2) Date: Sep. 20, 2016

(87) PCT Pub. No.: WO2015/140479
PCT Pub. Date: Sep. 24, 2015

(65) Prior Publication Data
US 2017/0137817 A1 May 18, 2017

(30) Foreign Application Priority Data

Mar. 20, 2014 (FR) ..................... 14 52345

(51) Int. Cl.
C12N 15/115 (2010.01)
G01N 33/574 (2006.01)

(52) U.S. Cl.
CPC ..... *C12N 15/115* (2013.01); *G01N 33/57496* (2013.01); *C12N 2310/16* (2013.01)

(58) Field of Classification Search
None
See application file for complete search history.

(56) References Cited

PUBLICATIONS

Kang, et al. (2008) "Characterization of PEGylated Anti-VEGF Aptamers Using Surface Plasmon Resonance", Macromolecular Research, 16(2): 182-84.*
Yan, et al. (2016) "Structure Prediction: New Insights into Decrypting Long Noncoding RNAs", International Journal of Molecular Sciences, 17(1): 132, 25 pages long.*
Ling H. (2016) Non-coding RNAs: Therapeutic Strategies and Delivery Systems. In: Slaby O., Calin G. (eds) Non-coding RNAs in Colorectal Cancer. Advances in Experimental Medicine and Biology, vol. 937. Springer, Cham.*
Loussouarn C et al: "Selection of DNA aptamers regulating STAT5B, a protein involved in leukemias", FEBS Journal, vol. 280, No. Suppl. 1, Sp. Iss. SI, Jul. 2013 (Jul. 1, 2013), pp. 320, XP002729464.
E. A. Nelson et al: "The STAT5 Inhibitor Pimozide Displays Efficacy in Models of Acute Myelogenous Leukemia Driven by FLT3 Mutations", Genes & Cancer, vol. 3, No. 7-8, Jul. 1, 2012 (Jul. 1, 2012), pp. 503-511, XP055137993, ISSN: 1947-6019, DOI: 10.1177/1947601912466555.
Brent D. G. Page et al: "Small Molecule STAT5-SH2 Domain Inhibitors Exhibit Potent Antileukemia Activity", Journal of Medicinal Chemistry, vol. 55, No. 3, Feb. 9, 2012 (Feb. 9, 2012), pp. 1047-1055, XP055137989, ISSN: 0022-2623, DOI: 10.1021/jm200720n.
F. Behbod et al: "Specific Inhibition of Stat5a/b Promotes Apoptosis of IL-2-Responsive Primary and Tumor-Derived Lymphoid Cells", The Journal of Immunology, vol. 171, No. 8, Oct. 6, 2003 (Oct. 6, 2003), pp. 3919-3927, XP055137991, ISSN: 0022-1767, DOI: 10.4049/jimmunol.171.8.3919.
Benekli Mustafa et al: "Signal transducer and activator of transcription proteins in leukemias.", Blood, vol. 101, No. 8, Apr. 15, 2003 (Apr. 15, 2003), pp. 2940-2954, XP055137992, ISSN: 0006-4971.
Stoltenburg R et al: "FluMag-SELEX as an advantageous method for DNA aptamer selection", Analytical and Bioanalytical Chemistry, vol. 383, Jul. 29, 2005 (Jul. 29, 2005), pp. 83-91, XP002408446, ISSN: 1618-2642, DOI: 10.1007/S00216-005-3388-9.
Axel Weber et al: "The Inhibition of Stat5 by a Peptide Aptamer Ligand Specific for the DNA Binding Domain Prevents Target Gene Transactivation and the Growth of Breast and Prostate Tumor Cells", Pharmaceuticals, vol. 6, No. 8, Aug. 20, 2013 (Aug. 20, 2013), pp. 960-987, XP055138067, DOI: 10.3390/ph6080960.
Futami et al, "RNAi-mediated silencing of p190Bcr-Abl inactivates Stat5 and cooperates with imatinib mesylate and 17-allylamino-17-demetoxygeldanamycin in selective killing of p190Bcr-Abl-expressing leukemia cells" Leukemia. 2008, 22(6):1131-8.
Mathews et al, "Expanded Sequence Dependence of Thermodynamic Parameters Improves Prediction of RNA Secondary Structure" J Mol Biol. 1999, 288 :911-940.

* cited by examiner

Primary Examiner — Robert M Kelly
(74) Attorney, Agent, or Firm — Heslin Rothenberg Farley & Mesiti P.C.

(57) ABSTRACT

Provided is a composition of matter binding specifically to STAT5, preferably to STAT5B, including a nucleic acid aptamer, and methods of treatment of cancer, and in particular leukaemia via the inhibition of STAT5 protein. The present invention relates more particularly to specific aptamers of STAT5 protein, and the therapeutic or diagnostic use thereof. Also provided is a method for detecting STAT5 in a biological sample, including contacting a nucleic acid aptamer binding specifically to STAT5 with a sample taken beforehand from a subject and determining the quantity of said aptamer bound to said sample.

7 Claims, 10 Drawing Sheets
Specification includes a Sequence Listing.

A

A: Charged strands
F: Fluorescent strands
E: Excess primers

B

SEQUENCE LISTING

```
<160> NUMBER OF SEQ ID NOS: 84

<210> SEQ ID NO 1
<211> LENGTH: 60
<212> TYPE: DNA
<213> ORGANISM: Artificial Sequence
<220> FEATURE:
<221> NAME/KEY: source
<222> LOCATION: 1..60
<223> OTHER INFORMATION: /mol_type="unassigned DNA"
      /note="Aptamer Apta 1"
      /organism="Artificial Sequence"

<400> SEQUENCE: 1
tatccgcaac ccacctagcg ccctacctcg tgggaatcca aacccaacca gtccacccac    60

<210> SEQ ID NO 2
<211> LENGTH: 60
<212> TYPE: DNA
<213> ORGANISM: Artificial Sequence
<220> FEATURE:
<221> NAME/KEY: source
<222> LOCATION: 1..60
<223> OTHER INFORMATION: /mol_type="unassigned DNA"
```

```
                /note="Aptamer Apta 2"
                /organism="Artificial Sequence"

<400> SEQUENCE: 2
gtgtctgttc actcgtcgat acacagcata ctcaacccag gccctgact gctaatcccc      60

<210> SEQ ID NO 3
<211> LENGTH: 96
<212> TYPE: DNA
<213> ORGANISM: Artificial Sequence
<220> FEATURE:
<221> NAME/KEY: source
<222> LOCATION: 1..96
<223> OTHER INFORMATION: /mol_type="unassigned DNA"
                /note="Aptamer Apta 1 and flanking sequences"
                /organism="Artificial Sequence"

<400> SEQUENCE: 3
ataccagctt attcaattta tccgcaaccc acctagcgcc ctacctcgtg ggaatccaaa      60
cccaaccagt ccacccacag atagtaagtg caatct                               96

<210> SEQ ID NO 4
<211> LENGTH: 96
<212> TYPE: DNA
<213> ORGANISM: Artificial Sequence
<220> FEATURE:
<221> NAME/KEY: source
<222> LOCATION: 1..96
<223> OTHER INFORMATION: /mol_type="unassigned DNA"
                /note="Aptamer Apta 2 and flanking sequences"
                /organism="Artificial Sequence"

<400> SEQUENCE: 4
ataccagctt attcaattgt gtctgttcac tcgtcgatac acagcatact caacccaggc      60
ccctgactgc taatccccag atagtaagtg caatct                               96

<210> SEQ ID NO 5
<211> LENGTH: 794
<212> TYPE: PRT
<213> ORGANISM: Homo sapiens
<220> FEATURE:
<223> OTHER INFORMATION: STAT5A

<400> SEQUENCE: 5

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
                20                  25                  30

Tyr Leu Ala Gln Trp Ile Glu Ser Gln Pro Trp Asp Ala Ile Asp Leu
            35                  40                  45

Asp Asn Pro Gln Asp Arg Ala Gln Ala Thr Gln Leu Leu Glu Gly Leu
        50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95

Thr Tyr Asp Arg Cys Pro Leu Glu Leu Val Arg Cys Ile Arg His Ile
                100                 105                 110

Leu Tyr Asn Glu Gln Arg Leu Val Arg Glu Ala Asn Asn Cys Ser Ser
            115                 120                 125

Pro Ala Gly Ile Leu Val Asp Ala Met Ser Gln Lys His Leu Gln Ile
        130                 135                 140
```

```
Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
            165                 170                 175

Gln Glu Ser Leu Arg Ile Gln Ala Gln Phe Ala Gln Leu Ala Gln Leu
        180                 185                 190

Ser Pro Gln Glu Arg Leu Ser Arg Glu Thr Ala Leu Gln Gln Lys Gln
            195                 200                 205

Val Ser Leu Glu Ala Trp Leu Gln Arg Glu Ala Gln Thr Leu Gln Gln
210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Glu Gly Ser Leu
                260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu His Leu Cys Gln Gln Leu Pro
290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
        370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
        435                 440                 445

Ser Val Gly Ser Asn Glu Leu Val Phe Gln Val Lys Thr Leu Ser Leu
        450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
            530                 535                 540

Leu Glu Asp Tyr Ser Gly Leu Ser Val Ser Trp Ser Gln Phe Asn Arg
545                 550                 555                 560
```

```
Glu Asn Leu Pro Gly Trp Asn Tyr Thr Phe Trp Gln Trp Phe Asp Gly
                    565                 570                 575
Val Met Glu Val Leu Lys Lys His His Lys Pro His Trp Asn Asp Gly
            580                 585                 590
Ala Ile Leu Gly Phe Val Asn Lys Gln Gln Ala His Asp Leu Leu Ile
        595                 600                 605
Asn Lys Pro Asp Gly Thr Phe Leu Leu Arg Phe Ser Asp Ser Glu Ile
    610                 615                 620
Gly Gly Ile Thr Ile Ala Trp Lys Phe Asp Ser Pro Glu Arg Asn Leu
625                 630                 635                 640
Trp Asn Leu Lys Pro Phe Thr Thr Arg Asp Phe Ser Ile Arg Ser Leu
                645                 650                 655
Ala Asp Arg Leu Gly Asp Leu Ser Tyr Leu Ile Tyr Val Phe Pro Asp
            660                 665                 670
Arg Pro Lys Asp Glu Val Phe Ser Lys Tyr Tyr Thr Pro Val Leu Ala
        675                 680                 685
Lys Ala Val Asp Gly Tyr Val Lys Pro Gln Ile Lys Gln Val Val Pro
    690                 695                 700
Glu Phe Val Asn Ala Ser Ala Asp Ala Gly Gly Ser Ser Ala Thr Tyr
705                 710                 715                 720
Met Asp Gln Ala Pro Ser Pro Ala Val Cys Pro Gln Ala Pro Tyr Asn
                725                 730                 735
Met Tyr Pro Gln Asn Pro Asp His Val Leu Asp Gln Asp Gly Glu Phe
            740                 745                 750
Asp Leu Asp Glu Thr Met Asp Val Ala Arg His Val Glu Glu Leu Leu
        755                 760                 765
Arg Arg Pro Met Asp Ser Leu Asp Ser Arg Leu Ser Pro Pro Ala Gly
    770                 775                 780
Leu Phe Thr Ser Ala Arg Gly Ser Leu Ser
785                 790

<210> SEQ ID NO 6
<211> LENGTH: 787
<212> TYPE: PRT
<213> ORGANISM: Homo sapiens
<220> FEATURE:
<223> OTHER INFORMATION: STAT5B

<400> SEQUENCE: 6

Met Ala Val Trp Ile Gln Ala Gln Gln Leu Gln Gly Glu Ala Leu His
1               5                   10                  15
Gln Met Gln Ala Leu Tyr Gly Gln His Phe Pro Ile Glu Val Arg His
            20                  25                  30
Tyr Leu Ser Gln Trp Ile Glu Ser Gln Ala Trp Asp Ser Val Asp Leu
        35                  40                  45
Asp Asn Pro Gln Glu Asn Ile Lys Ala Thr Gln Leu Leu Glu Gly Leu
    50                  55                  60
Val Gln Glu Leu Gln Lys Lys Ala Glu His Gln Val Gly Glu Asp Gly
65                  70                  75                  80
Phe Leu Leu Lys Ile Lys Leu Gly His Tyr Ala Thr Gln Leu Gln Asn
                85                  90                  95
Thr Tyr Asp Arg Cys Pro Met Glu Leu Val Arg Cys Ile Arg His Ile
            100                 105                 110
Leu Tyr Asn Glu Gln Arg Leu Val Arg Glu Ala Asn Asn Gly Ser Ser
        115                 120                 125
```

```
Pro Ala Gly Ser Leu Ala Asp Ala Met Ser Gln Lys His Leu Gln Ile
            130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Gly Pro Leu Ala Gln Leu
            180                 185                 190

Ser Pro Gln Glu Arg Leu Ser Arg Glu Thr Ala Leu Gln Gln Lys Gln
            195                 200                 205

Val Ser Leu Glu Ala Trp Leu Gln Arg Glu Ala Gln Thr Leu Gln Gln
210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
            275                 280                 285

Asn Arg Gln Gln Ile Arg Arg Ala Glu His Leu Cys Gln Gln Leu Pro
290                 295                 300

Ile Pro Gly Pro Val Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
370                 375                 380

Asn Glu Asn Thr Arg Asn Asp Tyr Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ser Asp Arg Arg Gly Ala
            420                 425                 430

Glu Ser Val Thr Glu Glu Lys Phe Thr Ile Leu Phe Glu Ser Gln Phe
            435                 440                 445

Ser Val Gly Gly Asn Glu Leu Val Phe Gln Val Lys Thr Leu Ser Leu
450                 455                 460

Pro Val Val Ile Val His Gly Ser Gln Asp Asn Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
530                 535                 540

Leu Glu Asp Tyr Ser Gly Leu Ser Val Ser Trp Ser Gln Phe Asn Arg
```

```
            545                 550                 555                 560
      Glu Asn Leu Pro Gly Arg Asn Tyr Thr Phe Trp Gln Trp Phe Asp Gly
                      565                 570                 575

Val Met Glu Val Leu Lys Lys His Leu Lys Pro His Trp Asn Asp Gly
                      580                 585                 590

Ala Ile Leu Gly Phe Val Asn Lys Gln Gln Ala His Asp Leu Leu Ile
                      595                 600                 605

Asn Lys Pro Asp Gly Thr Phe Leu Leu Arg Phe Ser Asp Ser Glu Ile
                  610                 615                 620

Gly Gly Ile Thr Ile Ala Trp Lys Phe Asp Ser Gln Glu Arg Met Phe
      625                 630                 635                 640

Trp Asn Leu Met Pro Phe Thr Thr Arg Asp Phe Ser Ile Arg Ser Leu
                          645                 650                 655

Ala Asp Arg Leu Gly Asp Leu Asn Tyr Leu Ile Tyr Val Phe Pro Asp
                      660                 665                 670

Arg Pro Lys Asp Glu Val Tyr Ser Lys Tyr Tyr Thr Pro Val Pro Cys
                      675                 680                 685

Glu Ser Ala Thr Ala Lys Ala Val Asp Gly Tyr Val Lys Pro Gln Ile
                  690                 695                 700

Lys Gln Val Val Pro Glu Phe Val Asn Ala Ser Ala Asp Ala Gly Gly
      705                 710                 715                 720

Gly Ser Ala Thr Tyr Met Asp Gln Ala Pro Ser Pro Ala Val Cys Pro
                          725                 730                 735

Gln Ala His Tyr Asn Met Tyr Pro Gln Asn Pro Asp Ser Val Leu Asp
                      740                 745                 750

Thr Asp Gly Asp Phe Asp Leu Glu Asp Thr Met Asp Val Ala Arg Arg
                      755                 760                 765

Val Glu Glu Leu Leu Gly Arg Pro Met Asp Ser Gln Trp Ile Pro His
      770                 775                 780

Ala Gln Ser
      785

<210> SEQ ID NO 7
<211> LENGTH: 793
<212> TYPE: PRT
<213> ORGANISM: Mus musculus
<220> FEATURE:
<223> OTHER INFORMATION: STAT5A

<400> SEQUENCE: 7

Met Ala Gly Trp Ile Gln Ala Gln Gln Leu Gln Gly Asp Ala Leu Arg
      1               5                   10                  15

Gln Met Gln Val Leu Tyr Gly Gln His Phe Pro Ile Glu Val Arg His
                      20                  25                  30

Tyr Leu Ala Gln Trp Ile Glu Ser Gln Pro Trp Asp Ala Ile Asp Leu
                  35                  40                  45

Asp Asn Pro Gln Asp Arg Gly Gln Ala Thr Gln Leu Leu Glu Gly Leu
              50                  55                  60

Val Gln Glu Leu Gln Lys Lys Ala Glu His Gln Val Gly Glu Asp Gly
      65                  70                  75                  80

Phe Leu Leu Lys Ile Lys Leu Gly His Tyr Ala Thr Gln Leu Gln Asn
                          85                  90                  95

Thr Tyr Asp Arg Cys Pro Met Glu Leu Val Arg Cys Ile Arg His Ile
                      100                 105                 110

Leu Tyr Asn Glu Gln Arg Leu Val Arg Glu Ala Asn Asn Cys Ser Ser
```

```
            115                 120                 125
Pro Ala Gly Val Leu Val Asp Ala Met Ser Gln Lys His Leu Gln Ile
130                 135                 140
Asn Gln Arg Phe Glu Glu Leu Arg Leu Ile Thr Gln Asp Thr Glu Asn
145                 150                 155                 160
Glu Leu Lys Lys Leu Gln Gln Thr Gln Glu Tyr Phe Ile Ile Gln Tyr
            165                 170                 175
Gln Glu Ser Leu Arg Ile Gln Ala Gln Phe Ala Gln Leu Gly Gln Leu
            180                 185                 190
Asn Pro Gln Glu Arg Met Ser Arg Glu Thr Ala Leu Gln Gln Lys Gln
            195                 200                 205
Val Ser Leu Glu Thr Trp Leu Gln Arg Glu Ala Gln Thr Leu Gln Gln
210                 215                 220
Tyr Arg Val Glu Leu Ala Glu Lys His Gln Lys Thr Leu Gln Leu Leu
225                 230                 235                 240
Arg Lys Gln Gln Thr Ile Ile Leu Asp Asp Glu Leu Ile Gln Trp Lys
            245                 250                 255
Arg Arg Gln Gln Leu Ala Gly Asn Gly Gly Pro Glu Gly Ser Leu
            260                 265                 270
Asp Val Leu Gln Ser Trp Cys Glu Lys Leu Ala Glu Ile Ile Trp Gln
            275                 280                 285
Asn Arg Gln Gln Ile Arg Arg Ala Glu His Leu Cys Gln Gln Leu Pro
290                 295                 300
Ile Pro Gly Pro Val Glu Glu Met Leu Ala Glu Val Asn Ala Thr Ile
305                 310                 315                 320
Thr Asp Ile Ile Ser Ala Leu Val Thr Ser Thr Phe Ile Ile Glu Lys
            325                 330                 335
Gln Pro Pro Gln Val Leu Lys Thr Gln Thr Lys Phe Ala Ala Thr Val
            340                 345                 350
Arg Leu Leu Val Gly Gly Lys Leu Asn Val His Met Asn Pro Pro Gln
            355                 360                 365
Val Lys Ala Thr Ile Ile Ser Glu Gln Gln Ala Lys Ser Leu Leu Lys
370                 375                 380
Asn Glu Asn Thr Arg Asn Glu Cys Ser Gly Glu Ile Leu Asn Asn Cys
385                 390                 395                 400
Cys Val Met Glu Tyr His Gln Ala Thr Gly Thr Leu Ser Ala His Phe
            405                 410                 415
Arg Asn Met Ser Leu Lys Arg Ile Lys Arg Ala Asp Arg Arg Gly Ala
            420                 425                 430
Glu Ser Val Thr Glu Glu Lys Phe Thr Val Leu Phe Glu Ser Gln Phe
            435                 440                 445
Ser Val Gly Ser Asn Glu Leu Val Phe Gln Val Lys Thr Leu Ser Leu
            450                 455                 460
Pro Val Val Val Ile Val His Gly Ser Gln Asp His Asn Ala Thr Ala
465                 470                 475                 480
Thr Val Leu Trp Asp Asn Ala Phe Ala Glu Pro Gly Arg Val Pro Phe
                485                 490                 495
Ala Val Pro Asp Lys Val Leu Trp Pro Gln Leu Cys Glu Ala Leu Asn
            500                 505                 510
Met Lys Phe Lys Ala Glu Val Gln Ser Asn Arg Gly Leu Thr Lys Glu
            515                 520                 525
Asn Leu Val Phe Leu Ala Gln Lys Leu Phe Asn Ile Ser Ser Asn His
            530                 535                 540
```

-continued

```
Leu Glu Asp Tyr Asn Ser Met Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Asn Tyr Leu Ile Tyr Val Phe Pro Asp
            660                 665                 670

Arg Pro Lys Asp Glu Val Phe Ala Lys Tyr Tyr Thr Pro Val Leu Ala
        675                 680                 685

Lys Ala Val Asp Gly Tyr Val Lys Pro Gln Ile Lys Gln Val Val Pro
    690                 695                 700

Glu Phe Val Asn Ala Ser Thr Asp Ala Gly Ala Ser Ala Thr Tyr Met
705                 710                 715                 720

Asp Gln Ala Pro Ser Pro Val Val Cys Pro Gln Pro His Tyr Asn Met
                725                 730                 735

Tyr Pro Pro Asn Pro Asp Pro Val Leu Asp Gln Asp Gly Glu Phe Asp
            740                 745                 750

Leu Asp Glu Ser Met Asp Val Ala Arg His Val Glu Glu Leu Leu Arg
        755                 760                 765

Arg Pro Met Asp Ser Leu Asp Ala Arg Leu Ser Pro Pro Ala Gly Leu
    770                 775                 780

Phe Thr Ser Ala Arg Ser Ser Leu Ser
785                 790
```

<210> SEQ ID NO 8
<211> LENGTH: 786
<212> TYPE: PRT
<213> ORGANISM: Mus musculus
<220> FEATURE:
<223> OTHER INFORMATION: STAT5B

<400> SEQUENCE: 8

```
Met Ala Met Trp Ile Gln Ala Gln Gln Leu Gln Gly Asp Ala Leu His
1               5                   10                  15

Gln Met Gln Ala Leu Tyr Gly Gln His Phe Pro Ile Glu Val Arg His
            20                  25                  30

Tyr Leu Ser Gln Trp Ile Glu Ser Gln Ala Trp Asp Ser Ile Asp Leu
        35                  40                  45

Asp Asn Pro Gln Glu Asn Ile Lys Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Ser
                85                  90                  95

Thr Tyr Asp Arg Cys Pro Met Glu Leu Val Arg Cys Ile Arg His Ile
            100                 105                 110
```

```
Leu Tyr Asn Glu Gln Arg Leu Val Arg Glu Ala Asn Gly Ser Ser
            115                 120                 125

Pro Ala Gly Ser Leu Ala Asp Ala Met Ser Gln Lys His Leu Gln Ile
    130                 135                 140

Asn Gln Thr Phe Glu Glu Leu Arg Leu Ile Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Gly Gln Leu
            180                 185                 190

Asn Pro Gln Glu Arg Met Ser Arg Glu Thr Ala Leu Gln Gln Lys Gln
        195                 200                 205

Val Ser Leu Glu Thr Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu His Leu Cys Gln Gln Leu Pro
    290                 295                 300

Ile Pro Gly Pro Val Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Asp Tyr Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ser Asp Arg Arg Gly Ala
            420                 425                 430

Glu Ser Val Thr Glu Glu Lys Phe Thr Ile Leu Phe Asp Ser Gln Phe
        435                 440                 445

Ser Val Gly Gly Asn Glu Leu Val Phe Gln Val Lys Thr Leu Ser Leu
    450                 455                 460

Pro Val Val Val Ile Val His Gly Ser Gln Asp Asn Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
        515                 520                 525
```

```
Asn Leu Val Phe Leu Ala Gln Lys Leu Phe Asn Ile Ser Ser Asn His
    530                 535                 540
Leu Glu Asp Tyr Asn Ser Met Ser Val Ser Trp Ser Gln Phe Asn Arg
545                 550                 555                 560
Glu Asn Leu Pro Gly Arg Asn Tyr Thr Phe Trp Gln Trp Phe Asp Gly
                565                 570                 575
Val Met Glu Val Leu Lys Lys His Leu Lys Pro His Trp Asn Asp Gly
            580                 585                 590
Ala Ile Leu Gly Phe Val Asn Lys Gln Gln Ala His Asp Leu Leu Ile
        595                 600                 605
Asn Lys Pro Asp Gly Thr Phe Leu Leu Arg Phe Ser Asp Ser Glu Ile
610                 615                 620
Gly Gly Ile Thr Ile Ala Trp Lys Phe Asp Ser Gln Glu Arg Met Phe
625                 630                 635                 640
Trp Asn Leu Met Pro Phe Thr Thr Arg Asp Phe Ser Ile Arg Ser Leu
                645                 650                 655
Ala Asp Arg Leu Gly Asp Leu Asn Tyr Leu Ile Tyr Val Phe Pro Asp
                660                 665                 670
Arg Pro Lys Asp Glu Val Tyr Ser Lys Tyr Tyr Thr Pro Val Pro Cys
            675                 680                 685
Glu Pro Ala Thr Ala Lys Ala Ala Asp Gly Tyr Val Lys Pro Gln Ile
690                 695                 700
Lys Gln Val Val Pro Glu Phe Ala Asn Ala Ser Thr Asp Ala Gly Ser
705                 710                 715                 720
Gly Ala Thr Tyr Met Asp Gln Ala Pro Ser Pro Val Val Cys Pro Gln
                725                 730                 735
Ala His Tyr Asn Met Tyr Pro Pro Asn Pro Asp Ser Val Leu Asp Thr
                740                 745                 750
Asp Gly Asp Phe Asp Leu Glu Asp Thr Met Asp Val Ala Arg Arg Val
            755                 760                 765
Glu Glu Leu Leu Gly Arg Pro Met Asp Ser Gln Trp Ile Pro His Ala
770                 775                 780
Gln Ser
785

<210> SEQ ID NO 9
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer STAT5 sens"
      /organism="Artificial Sequence"

<400> SEQUENCE: 9
ataccagctt attcaatt                                                 18

<210> SEQ ID NO 10
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer STAT5 antisens"
      /organism="Artificial Sequence"
```

```
<400> SEQUENCE: 10
agattgcact tactatct                                                18

<210> SEQ ID NO 11
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="fragment of Apta 1"
      /organism="Artificial Sequence"

<400> SEQUENCE: 11
gtgggaatcc aaacccaacc agtccaccca c                                 31

<210> SEQ ID NO 12
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 12
gtgggaatcc aaacccaacc agtccaccca ca                                32

<210> SEQ ID NO 13
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 13
gtgggaatcc aaacccaacc agtccaccca ct                                32

<210> SEQ ID NO 14
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 14
gtgggaatcc aaacccaacc agtccaccca cc                                32

<210> SEQ ID NO 15
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"
```

<400> SEQUENCE: 15
gtgggaatcc aaacccaacc agtccaccca cg                32

<210> SEQ ID NO 16
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 16
agtgggaatc aaacccaac cagtccaccc ac                 32

<210> SEQ ID NO 17
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 17
tgtgggaatc caaacccaac cagtccaccc ac                32

<210> SEQ ID NO 18
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 18
cgtgggaatc caaacccaac cagtccaccc ac                32

<210> SEQ ID NO 19
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="fragment of Apta 1"
      /organism="Artificial Sequence"

<400> SEQUENCE: 19
ggtgggaatc caaacccaac cagtccaccc ac                32

<210> SEQ ID NO 20
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="fragment of Apta 1"

-continued

/organism="Artificial Sequence"

<400> SEQUENCE: 20
gtgggaatcc aaacccaacc agtccaccca cat                33

<210> SEQ ID NO 21
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
     /note="fragment of Apta 1"
     /organism="Artificial Sequence"

<400> SEQUENCE: 21
gtgggaatcc aaacccaacc agtccaccca cac                33

<210> SEQ ID NO 22
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
     /note="fragment of Apta 1"
     /organism="Artificial Sequence"

<400> SEQUENCE: 22
gtgggaatcc aaacccaacc agtccaccca cag                33

<210> SEQ ID NO 23
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
     /note="fragment of Apta 1"
     /organism="Artificial Sequence"

<400> SEQUENCE: 23
gtgggaatcc aaacccaacc agtccaccca caa                33

<210> SEQ ID NO 24
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
     /note="fragment of Apta 1"
     /organism="Artificial Sequence"

<400> SEQUENCE: 24
gtgggaatcc aaacccaacc agtccaccca caca               34

<210> SEQ ID NO 25
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"

/note="fragment of Apta 1"
                              /organism="Artificial Sequence"

<400> SEQUENCE: 25
gtgggaatcc aaacccaacc agtccaccca cact                              34

<210> SEQ ID NO 26
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
                              /note="fragment of Apta 1"
                              /organism="Artificial Sequence"

<400> SEQUENCE: 26
gtgggaatcc aaacccaacc agtccaccca cacg                              34

<210> SEQ ID NO 27
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
                              /note="fragment of Apta 1"
                              /organism="Artificial Sequence"

<400> SEQUENCE: 27
gtgggaatcc aaacccaacc agtccaccca cacc                              34

<210> SEQ ID NO 28
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
                              /note="fragment of Apta 1"
                              /organism="Artificial Sequence"

<400> SEQUENCE: 28
gtgggaatcc taacccaacc agtccaccca c                                 31

<210> SEQ ID NO 29
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
                              /note="fragment of Apta 1"
                              /organism="Artificial Sequence"

<400> SEQUENCE: 29
gtgggaatcc aaacccaacc agtccagcca c                                 31

<210> SEQ ID NO 30
<211> LENGTH: 32
<212> TYPE: DNA
<213> ORGANISM: Artificial Sequence
<220> FEATURE:
<221> NAME/KEY: source
<222> LOCATION: 1..32

```
<223> OTHER INFORMATION: /mol_type="unassigned DNA"
        /note="fragment of Apta 1"
        /organism="Artificial Sequence"

<400> SEQUENCE: 30
gtgggaatcc aaatcccaac cagtccaccc ac                                    32

<210> SEQ ID NO 31
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
        /note="fragment of Apta 1"
        /organism="Artificial Sequence"

<400> SEQUENCE: 31
gtgggaatcc aaacccaacc gagtccaccc ac                                    32

<210> SEQ ID NO 32
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
        /note="fragment of Apta 2"
        /organism="Artificial Sequence"

<400> SEQUENCE: 32
ttgtgtctgt tcactcgtcg atacacag                                         28

<210> SEQ ID NO 33
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
        /note="fragment of Apta 2"
        /organism="Artificial Sequence"

<400> SEQUENCE: 33
ttgtgtctgt tcactcgtcg atacacaga                                        29

<210> SEQ ID NO 34
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
        /note="fragment of Apta 2"
        /organism="Artificial Sequence"

<400> SEQUENCE: 34
ttgtgtctgt tcactcgtcg atacacagt                                        29

<210> SEQ ID NO 35
<211> LENGTH: 29
<212> TYPE: DNA
<213> ORGANISM: Artificial Sequence
<220> FEATURE:
<221> NAME/KEY: source
```

```
<222> LOCATION: 1..29
<223> OTHER INFORMATION: /mol_type="unassigned DNA"
      /note="fragment of Apta 2"
      /organism="Artificial Sequence"

<400> SEQUENCE: 35
ttgtgtctgt tcactcgtcg atacacagc                              29

<210> SEQ ID NO 36
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 36
ttgtgtctgt tcactcgtcg atacacagg                              29

<210> SEQ ID NO 37
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 37
attgtgtctg ttcactcgtc gatacacag                              29

<210> SEQ ID NO 38
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 38
cttgtgtctg ttcactcgtc gatacacag                              29

<210> SEQ ID NO 39
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 39
gttgtgtctg ttcactcgtc gatacacag                              29

<210> SEQ ID NO 40
<211> LENGTH: 29
<212> TYPE: DNA
<213> ORGANISM: Artificial Sequence
<220> FEATURE:
```

```
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 40
tttgtgtctg ttcactcgtc gatacacag                                    29

<210> SEQ ID NO 41
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 41
aattgtgtct gttcactcgt cgatacacag                                   30

<210> SEQ ID NO 42
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 42
tattgtgtct gttcactcgt cgatacacag                                   30

<210> SEQ ID NO 43
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 43
cattgtgtct gttcactcgt cgatacacag                                   30

<210> SEQ ID NO 44
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment Apta 2"
      /organism="Artificial Sequence"

<400> SEQUENCE: 44
gattgtgtct gttcactcgt cgatacacag                                   30

<210> SEQ ID NO 45
<211> LENGTH: 30
<212> TYPE: DNA
<213> ORGANISM: Artificial Sequence
```

```
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 45
ttgtgtctgt tcactcgtcg atacacagaa                              30

<210> SEQ ID NO 46
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 46
ttgtgtctgt tcactcgtcg atacacagat                              30

<210> SEQ ID NO 47
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 47
ttgtgtctgt tcactcgtcg atacacagac                              30

<210> SEQ ID NO 48
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 48
ttgtgtctgt tcactcgtcg atacacagag                              30

<210> SEQ ID NO 49
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 49
ttgtgtctgt tcactcgtcg atacacagta                              30

<210> SEQ ID NO 50
<211> LENGTH: 30
<212> TYPE: DNA
```

```
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 50
ttgtgtctgt tcactcgtcg atacacagtt                                30

<210> SEQ ID NO 51
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 1"
      /organism="Artificial Sequence"

<400> SEQUENCE: 51
ttgtgtctgt tcactcgtcg atacacagtc                                30

<210> SEQ ID NO 52
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 2"
      /organism="Artificial Sequence"

<400> SEQUENCE: 52
ttgtgtctgt tcactcgtcg atacacagtg                                30

<210> SEQ ID NO 53
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="fragment of Apta 2"
      /organism="Artificial Sequence"

<400> SEQUENCE: 53
ttgtgtctgt acactcgtcg atacacag                                  28

<210> SEQ ID NO 54
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="fragment of Apta 2"
      /organism="Artificial Sequence"

<400> SEQUENCE: 54
ttgtgtctgt tcactcctcg atacacag                                  28

<210> SEQ ID NO 55
<211> LENGTH: 29
```

<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 55
ttgtgtctgt tcaactcgtc gatacacag                              29

<210> SEQ ID NO 56
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 2"
      /organism="Artificial Sequence"

<400> SEQUENCE: 56
ttgtgtctgt tcactcgtcg gatacacag                              29

<210> SEQ ID NO 57
<211> LENGTH: 60
<212> TYPE: DNA
<213> ORGANISM: Artificial Sequence
<220> FEATURE:
<221> NAME/KEY: source
<222> LOCATION: 1..60
<223> OTHER INFORMATION: /mol_type="unassigned DNA"
      /note="Aptamer Apta 3"
      /organism="Artificial Sequence"

<400> SEQUENCE: 57
gtgtctgttc actcgtcgat acacaacata ctcaacccag gccctgact gctaatcccc    60

<210> SEQ ID NO 58
<211> LENGTH: 96
<212> TYPE: DNA
<213> ORGANISM: Artificial Sequence
<220> FEATURE:
<221> NAME/KEY: source
<222> LOCATION: 1..96
<223> OTHER INFORMATION: /mol_type="unassigned DNA"
      /note="Aptamer Apta 3 and flanking sequences"
      /organism="Artificial Sequence"

<400> SEQUENCE: 58
ataccagctt attcaattgt gtctgttcac tcgtcgatac acaacatact caacccaggc    60
ccctgactgc taatcccag atagtaagtg caatct                              96

<210> SEQ ID NO 59
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="fragment of Apta 3"
      /organism="Artificial Sequence"

<400> SEQUENCE: 59
ttgtgtctgt tcactcgtcg atacacaa                               28

```
<210> SEQ ID NO 60
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 60
ttgtgtctgt tcactcgtcg atacacaaa                                29

<210> SEQ ID NO 61
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 61
ttgtgtctgt tcactcgtcg atacacaat                                29

<210> SEQ ID NO 62
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 62
ttgtgtctgt tcactcgtcg atacacaac                                29

<210> SEQ ID NO 63
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 63
ttgtgtctgt tcactcgtcg atacacaag                                29

<210> SEQ ID NO 64
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 64
attgtgtctg ttcactcgtc gatacacaa                                29
```

<210> SEQ ID NO 65
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 65
cttgtgtctg ttcactcgtc gatacacaa                                29

<210> SEQ ID NO 66
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 66
gttgtgtctg ttcactcgtc gatacacaa                                29

<210> SEQ ID NO 67
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 67
tttgtgtctg ttcactcgtc gatacacaa                                29

<210> SEQ ID NO 68
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 68
aattgtgtct gttcactcgt cgatacacaa                               30

<210> SEQ ID NO 69
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 69
tattgtgtct gttcactcgt cgatacacaa                                        30

<210> SEQ ID NO 70
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 70
cattgtgtct gttcactcgt cgatacacaa                                        30

<210> SEQ ID NO 71
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 71
gattgtgtct gttcactcgt cgatacacaa                                        30

<210> SEQ ID NO 72
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 72
ttgtgtctgt tcactcgtcg atacacaaaa                                        30

<210> SEQ ID NO 73
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 73
ttgtgtctgt tcactcgtcg atacacaaat                                        30

<210> SEQ ID NO 74
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 74
ttgtgtctgt tcactcgtcg atacacaaac                                          30

<210> SEQ ID NO 75
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 75
ttgtgtctgt tcactcgtcg atacacaaag                                          30

<210> SEQ ID NO 76
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 76
ttgtgtctgt tcactcgtcg atacacaata                                          30

<210> SEQ ID NO 77
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 77
ttgtgtctgt tcactcgtcg atacacaatt                                          30

<210> SEQ ID NO 78
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

<400> SEQUENCE: 78
ttgtgtctgt tcactcgtcg atacacaatc                                          30

<210> SEQ ID NO 79
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="fragment of Apta 3"
      /organism="Artificial Sequence"

```
<400> SEQUENCE: 79
ttgtgtctgt tcactcgtcg atacacaatg                                          30

<210> SEQ ID NO 80
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="fragment of Apta 3"
      /organism="Artificial Sequence"

<400> SEQUENCE: 80
ttgtgtctgt acactcgtcg atacacaa                                            28

<210> SEQ ID NO 81
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="fragment of Apta 3"
      /organism="Artificial Sequence"

<400> SEQUENCE: 81
ttgtgtctgt tcactcctcg atacacaa                                            28

<210> SEQ ID NO 82
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 82
ttgtgtctgt tcaactcgtc gatacacaa                                           29

<210> SEQ ID NO 83
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="fragment of Apta 3"
      /organism="Artificial Sequence"

<400> SEQUENCE: 83
ttgtgtctgt tcactcgtcg gatacacaa                                           29

<210> SEQ ID NO 84
<211> LENGTH: 96
<212> TYPE: DNA
<213> ORGANISM: Artificial Sequence
<220> FEATURE:
<221> NAME/KEY: source
<222> LOCATION: 1..96
<223> OTHER INFORMATION: /mol_type="unassigned DNA"
      /note="random library of oligonucleotides"
      /organism="Artificial Sequence"
```

```
<220> FEATURE:
<221> NAME/KEY: misc_feature
<222> LOCATION: 19..78
<223> OTHER INFORMATION: /note="n est A, T, G ou C"

<400> SEQUENCE: 84
ataccagctt attcaattnn nnnnnnnnnn nnnnnnnnnn nnnnnnnnnn nnnnnnnnnn      60
nnnnnnnnnn nnnnnnnnag atagtaagtg caatct                               96
```

＃ STAT5 INHIBITORS AND USE THEREOF

CROSS REFERENCE TO RELATED APPLICATIONS

This application is a national stage filing under section 371 of International Application No. PCT/FR2015/050711, filed on Mar. 20, 2015, and published in French on Sep. 24, 2015, as WO 2015/140479 A1 and claims priority of French application no. 1452345 filed on Mar. 20, 2014, the entire disclosure of these applications being hereby incorporated herein by reference.

FIELD OF THE INVENTION

This invention relates to the treatment of cancer, and in particular leukaemia via the inhibition of STAT5 protein. This invention relates more particularly to specific aptamers of STAT5 protein, and the therapeutic or diagnostic use thereof.

BACKGROUND OF INVENTION

The objective of this invention is to suggest a new molecule which could enter into a therapeutic process for cancers, in particular leukaemias and myeloproliferative neoplasms. Leukaemias and myeloproliferative neoplasms are currently the most frequent cases of cancer with high mortality in men younger than 40 years old and in women younger than 20 years old. One of the recognised markers of these diseases is the malfunction of the transcription factor (TF) Signal Transducer and Activator of Transcription 5 (STAT5) which refers to two proteins, STAT5A and STAT5B which belong to the STAT family of proteins comprising 7 members. STAT5A and STAT5B proteins are encoded by 2 separate genes but their amino acid sequence is identical by more than 90%. STAT5 proteins are involved in cytosolic signalling pathways. Studies have shown that a malfunction of the activity of STAT5A and STAT5B could contribute to the induction of human cancers.

The activation of STAT5B proteins is frequently found in cases of haematological malignancies. In this context, STAT5B protein has been shown as being responsible for leukemogenesis (Benekli et al, 2003 Blood. 101 (8), 2940-54). Studies have also shown that STAT5 transcription factors were activated by a wide spectrum of ligands allowing them to intervene in the physiological and pathophysiological regulation of major biological functions such as cell proliferation, cell differentiation or apoptosis. STAT5B protein therefore constitutes a promising target for new anti-cancer treatments. From an application point of view, the obtaining of molecules that inhibit the activity of STAT5B protein is all the more so important when it is known that the current treatments are not very specific and cause undesirable side effects.

Indeed, treatments such as radiation or chemotherapy are heavy treatments that require long hospital stays in certain cases. Certain patients develop a resistance to the pharmacological inhibitor Imatinib mesylate (or Glivec®—Novartis) currently used as a first line clinically in certain cases of leukaemia. It is therefore indispensable to develop new compounds that make it possible to treat these diseases.

STAT5 inhibitors have already been developed such as AZD1480 but it is also an inhibitor of STAT3 and has side effects. Pimozide inhibits STAT5 but is also a dopamine receptor antagonist and consequently an antipsychotic (Nelson E A Genes Cancer 2012 July; 3(7-8):503-11). Antisenses for STAT5 AB have been tested in vitro in fundamental work but have not yet been developed or tested in clinical trials (Behbod F 2003 J Immunol 171(8):3919-27; Futami M Leukaemia. 2008 June; 22(6):1131-8; Page B D et al 2011 J Med Chem. 2012 Feb. 9; 55(3):1047-55).

In this invention, new specific aptamers of STAT5 protein are described. These aptamers have the advantage of inhibiting STAT5 protein as far downstream as possible of the signalling pathway so as to prevent undesirable side effects that could be linked to the inhibition of the expression of STAT5 protein. Indeed, STAT5 protein is involved in various processes and at different levels in the signalling pathways and the globalised inhibition thereof could be deleterious for the cell. The molecules also have the advantage of being highly specific for the targeted protein, and poorly immunogenic, and demonstrate effective anti-proliferative and pro-apoptotic properties (see the examples).

SUMMARY

One object of the invention is a nucleic acid aptamer binding specifically to STAT5, preferably to STAT5B, said aptamer being characterised in that it comprises the sequence SEQ ID NO: 1 or SEQ ID NO: 2 or SEQ ID NO: 57, or a fragment of the latter, or a variant that has at least 70% of sequence identity with SEQ ID NO: 1 or SEQ ID NO: 2 or SEQ ID NO: 57.

In one embodiment, said aptamer further comprises an additional stabilisation group and/or an additional group for vectorisation.

Another object of the invention is a pharmaceutical composition comprising at least one aptamer such as described hereinabove and a pharmaceutically acceptable excipient.

Another object of the invention is a medicament comprising at least one aptamer such as described hereinabove.

The invention also has for object an aptamer, a pharmaceutical composition or a medicament such as described hereinabove for their use in the treatment of cancers, preferably leukaemia.

In one embodiment, the aptamer or the pharmaceutical composition or the medicament of the invention is used in combination with another active agent selected from anti-cancer agents, anti-angiogenic agents, anti-metastatic agents, anti-leukemic agents, anti-folic agents, anti-metabolite agents, alkylating agents, intercalating agents, agents acting on the mitotic spindle, tyrosine kinase inhibitors, differentiating agents, or a mixture thereof.

In another embodiment, the aptamer of the invention is in combination with another active agent selected from anti-cancer agents, anti-angiogenic agents, anti-metastatic agents, anti-leukemic agents, anti-folic agents, anti-metabolite agents, alkylating agents, intercalating agents, agents acting on the mitotic spindle, tyrosine kinase inhibitors, differentiating agents, or a mixture thereof, for its use in the treatment of cancers, preferably leukaemia.

In another embodiment, the pharmaceutical composition or the medicament of the invention is in combination with another active agent selected from anti-cancer agents, anti-angiogenic agents, anti-metastatic agents, anti-leukemic agents, anti-folic agents, anti-metabolite agents, alkylating agents, intercalating agents, agents acting on the mitotic spindle, tyrosine kinase inhibitors, differentiating agents, or a mixture thereof, for its use in the treatment of cancers, preferably leukaemia.

The invention also has for object a method for detecting STAT5 in a biological sample comprising:

a. contacting of the aptamer such as described hereinabove with said sample taken beforehand from a subject;
b. the determining of the quantity of said aptamer bound to said sample.

DEFINITIONS

In the present invention, the following terms have the following meanings:

"Aptamer" relates to an isolated oligonucleotide and can also indifferently be designated in this invention as "nucleic acid aptamer". The aptamer or the nucleic acid aptamer is a single-strand or double-strand oligonucleotide sequence that can be bound to a protein or other molecule, and as such disturbing the function of said protein or other molecule. In an embodiment, the nucleic acid comprises ribonucleoside units.

In the meaning of the present invention, the terms "treatment", "treat" or "alleviate" relate both to the therapeutic treatment and prophylactic or preventive measures, of which the object is to prevent or delay the appearance or the installation of a cancer. The subjects to be treated therefore include both subjects already afflicted with cancer, and subjects predisposed to develop cancer or subjects for which such a disease must be prevented. A subject is effectively "treated" for a cancer if, after having received a therapeutically effective amount of an aptamer according to the invention, said subject shows an observable and/or measurable improvement in the number of cancer cells, and/or a notable improvement in their quality of life. These parameters for evaluating an effective treatment can be measured easily with routine procedures familiar to those skilled in the art.

In the meaning of the present invention, the expression "effective amount" (or "therapeutically effective amount") refers to an amount of the aptamer according to the invention that is required or that is sufficient to, without causing significant and undesirable side effects for the subject, (1) delay or stop the appearance of a cancer, (2) provide improvements, (3) reduce the severity of the incidence of a cancer, or (4) stop or care for a cancer. An effective amount can be administered before the appearance of a cancer, for a prophylactic or preventive action. Alternatively or additionally, an effective amount can be administered after the appearance of a cancer, for a therapeutic action.

An "excipient" designates, in this invention, any substance other than the active principle present in a composition that confers upon it properties of stability, form (liquid, solid, capsule, etc. according to the mode of administration), taste, dissolution (for example targeted dissolution in the stomach or digestive tract), colour, etc. A "pharmaceutically acceptable excipient" designates more specifically an excipient that does not induce an allergic or undesired reaction or when it is administered to a subject, more preferably to a human. This definition includes all the solvents, dispersion mediums, coatings, antibacterial and antifungal agents, isotonic agents and agents that make it possible to delay the absorption of the active principle, etc. For administration for humans, the preparations must satisfy the conditions of sterility, pyrogenicity, general safety and purity standards defined by the biological standards bureau of the FDA.

"About": preceding a figure means plus or less 10% of the value of said figure.

"Specific": which is bound specifically to the target protein and which enhances a biological effect or on the contrary blocks the biological effect of the target protein. This binding is saturable while a non-specific binding does not trigger any biological effect that can be measured and is non-saturable. An aptamer is said to bind specifically to a target when it does not substantially have any affinity for a compound without any structural relationship with the target. Preferably, in the case of a protein target, a protein compound is said to be without structural relationship with the target according to the invention, when the sequence identity between the target and the compound is less than 60%, preferably less than 70%, more preferably less than 80%.

DETAILED DESCRIPTION

This invention relates to nucleic acid aptamers binding specifically to STAT5.

The specific interaction between an aptamer and the target protein can be determined by the Test A such as described in the example 2 of this invention.

200 pmol of biotinylated aptamers are incubated with 200 µg of proteins of cytoplasmic and nuclear extracts for 2 h over ice in the binding/washing buffer (5×: Tris pH 7.5 50 mM; NaCl 50 mM; EDTA 5 mM; PMSF 2.5 mM; Glycerol 25%; NP40—Tergitol® 0.5%). The mixture is then put into contact with 100 µL of streptavidin beads (Dynal) for 30 minutes under agitation at 4° C. The whole is washed 3 times with the washing buffer. The proteins are then eluted by adding 40 µL of elution buffer (Tris 0.5 M 250 mM pH 6.8; Glycerol 25%, SDS 8%, (3-mercaptoethanol 20%; $H_2O$ qsp 10 mL) and by heating 5 minutes at 90° C.

The proteins are analysed by Western Blot after electrophoretic migration on SDS-PAGE gel.

Activated STAT5 proteins are detected by using two antibodies (at the concentrations indicated by the supplier): Antibody anti-STAT5 (C-17 Santa Cruz) produced in rabbits; Antibody anti-PhosphoSTAT5 (Y694) produced in rabbits (Cell Signalling).

The specific recognition of these antibodies is then revealed by a secondary antibody (anti-rabbit IgG) marked with peroxidase (Sigma-Aldrich) diluted to 1/5000.

In one embodiment, an aptamer is said to not have substantially any affinity for a compound according to the invention, in particular when the dissociation constant ($K_D$) of aptamer with respect to a protein is greater than $10^{-6}$ mol/L, preferably greater than $10^{-7}$ mol/L. The dissociation constant can in particular be determined, in standard conditions, using Scatchard and Lineweaver Burk plots well known to those skilled in the art. Preferably, the affinity of the aptamer of the invention for a protein is of a $K_D$ from about 100 pM to about 10 nM.

In one embodiment, the aptamer of the invention modulates the STAT/Jak (Janus Kinase) signalling pathway. The dysregulation of the STAT/Jak signalling pathway is highly involved in the development of cancers. The dysregulation of the STAT/Jak signalling pathway is well known to those skilled in the art and can be measured in Western-Blot or ELISA tests making it possible to determine the level of the phosphorylation of the kinases involved in this path.

According to one embodiment, the aptamers of the invention bind specifically to human STAT5A protein (SEQ ID NO: 5) and human STAT5B protein (SEQ ID NO: 6), preferably STAT5B. According to another embodiment, the aptamers of the invention inhibit, preferably inhibit specifically, STAT5A (SEQ ID NO: 5) and STAT5B (SEQ ID NO: 6), preferably STAT5B.

As STAT5 protein intervenes at various levels of the transduction path of the signal, several inhibition possibilities are possible. In one embodiment, STAT5 is inhibited on cytoplasm when the protein is in monomeric form. In another embodiment, the inhibition intervenes during the process of dimerization and/or during the translocation of the latter to the nucleus as such preventing the fixing thereof on its target sequences. In another embodiment, the inhibition of STAT5 intervenes in order to prevent the fixing thereof on the gene promoter on the DNA. In another embodiment, the inhibition of STAT5 corresponds to the inhibition of its phosphorylation, and can be measured by techniques well known to those skilled in the art, such as, for example, a Western-Blot with for example, Antibody anti-STAT5 (C-17 Santa Cruz) produced in rabbits; Antibody anti-PhosphoSTAT5 (Y694) produced in rabbits (Cell Signalling).

The aptamer of the present invention comprises or consists of a sequence selected from the sequence Apta 1 (SEQ ID NO: 1), the sequence Apta 2 (SEQ ID NO: 2), the sequence Apta 3 (SEQ ID NO: 57), a fragment of Apta 1, a fragment of Apta 2, a fragment of Apta 3, a variant of Apta 1, a variant of Apta 2 or a variant of Apta 3.

SEQ ID NO: 1:
5'-TATCCGCAACCCACCTAGCGCCCTACCTCGTGGGAATCCAAACCCAA
CCAGTCCACCCAC-3'

SEQ ID NO: 2:
5'-GTGTCTGTTCACTCGTCGATACACAGCATACTCAACCCAGGCCCCTG
ACTGCTAATCCCC-3'

SEQ ID NO: 57:
5'-GTGTCTGTTCACTCGTCGATACACAACATACTCAACCCAGGCCCCTG
ACTGCTAATCCCC-3'.

In one embodiment, the aptamer of the present invention comprises or consists of a sequence selected from the sequences Apta 1, Apta 2 and Apta 3, a fragment or a variant of the latter framed in 5' and 3' by a flanking sequence.

In one embodiment, the aptamer of the present invention comprising SEQ ID NO: 1 or SEQ ID NO: 2 or SEQ ID NO: 57 according to the invention can in particular comprise sequences of the side 5' and/or 3' aiming to structure the nucleic acid such as flanking sequences. Preferentially, the aptamer according to the invention comprises, or is constituted of SEQ ID NO: 3 or 4 or 58, which include respectively SEQ ID NO: 1 and 2 and 57. In this embodiment, the invention then also relates, in particular, to an aptamer comprising, or constituted of at least 15 consecutive nucleotides of a sequence having at least 60% identity with SEQ ID NO: 3 or SEQ ID NO: 4 or SEQ ID NO: 58, with the condition that an aptamer present constituted of this sequence is bound specifically to STAT5.

SEQ ID NO: 3:
5'-ATACCAGCTTATTCAATT**TATCCGCAACCCACCTAGCGCCCTACCTC
GTGGGAATCCAAACCCAACCAGTCCACCCAC**AGATAGTAAGTGCAATC
T-3'.

SEQ ID NO: 4:
5'-ATACCAGCTTATTCAATT**GTGTCTGTTCACTCGTCGATACACAGCAT
ACTCAACCCAGGCCCCTGACTGCTAATCCCC**AGATAGTAAGTGCAATC
T-3'.

SEQ ID NO: 58:
5'-ATACCAGCTTATTCAATT**GTGTCTGTTCACTCGTCGATACACAACAT
ACTCAACCCAGGCCCCTGACTGCTAATCCCC**AGATAGTAAGTGCAATC
T-3'.

In one embodiment, a fragment of the aptamer of the invention comprises or consists in at least 15 consecutive nucleotides, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleotides of the sequences SEQ ID NO: 1 and 2 and 57.

In another embodiment, the variant of the aptamer of the invention comprises or consists of a sequence that has at least 60%, 65%, 70%, 75%, 80%, 85%, 90%, 95%, 96%, 97%, 98%, or 99% identity with SEQ ID NO: 1 or 2 or 57.

In another embodiment, the variant of the aptamer of the invention comprises or consists of a sequence of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides having at least 60%, 65%, 70%, 75%, 80%, 85%, 90%, 95%, 96%, 97%, 98%, or 99% identity with SEQ ID NO: 1 or 2 or 57.

In one embodiment, a fragment of the aptamer of this invention comprises or consists of a nucleotide sequence from 15 to 100 nucleotides, preferably from 20 to 60 nucleotides, more preferably from 25 to 40 nucleotides and having 70; 75; 80; 85; 90; 95; 96; 97; 98; 99% identity with SEQ ID NO: 1 or SEQ ID NO: 2 or SEQ ID NO: 57.

For example, a fragment of the aptamer of SEQ ID NO: 1 is:

(SEQ ID NO: 11)
5'-GTGGGAATCCAAACCCAACCAGTCCACCCAC-3';

(SEQ ID NO: 12)
5'-GTGGGAATCCAAACCCAACCAGTCCACCCACA-3';

(SEQ ID NO: 13)
5'-GTGGGAATCCAAACCCAACCAGTCCACCCACT-3';

(SEQ ID NO: 14)
5'-GTGGGAATCCAAACCCAACCAGTCCACCCACC-3';

(SEQ ID NO: 15)
5'-GTGGGAATCCAAACCCAACCAGTCCACCCACG-3';

(SEQ ID NO: 16)
5'-AGTGGGAATCCAAACCCAACCAGTCCACCCAC-3';

(SEQ ID NO: 17)
5'-TGTGGGAATCCAAACCCAACCAGTCCACCCAC-3';

(SEQ ID NO: 18)
5'-CGTGGGAATCCAAACCCAACCAGTCCACCCAC-3';

(SEQ ID NO: 19)
5'-GGTGGGAATCCAAACCCAACCAGTCCACCCAC-3';

(SEQ ID NO: 20)
5'-GTGGGAATCCAAACCCAACCAGTCCACCCACAT-3';

(SEQ ID NO: 21)
5'-GTGGGAATCCAAACCCAACCAGTCCACCCACAC-3';

(SEQ ID NO: 22)
5'-GTGGGAATCCAAACCCAACCAGTCCACCCACAG-3';

(SEQ ID NO: 23)
5'-GTGGGAATCCAAACCCAACCAGTCCACCCACAA-3';

(SEQ ID NO: 24)
5'-GTGGGAATCCAAACCCAACCAGTCCACCCACACA-3';

(SEQ ID NO: 25)
5'-GTGGGAATCCAAACCCAACCAGTCCACCCACACT-3';

(SEQ ID NO: 26)
5'-GTGGGAATCCAAACCCAACCAGTCCACCCACACG-3';

-continued

```
                                       (SEQ ID NO: 27)
5'-GTGGGAATCCAAACCCAACCAGTCCACCCACACC-3';

(SEQ ID NO: 28)
5'-GTGGGAATCCTAACCCAACCAGTCCACCCAC-3';

(SEQ ID NO: 29)
5'-GTGGGAATCCAAACCCAACCAGTCCAGCCAC-3';

(SEQ ID NO: 30)
5'-GTGGGAATCCAAATCCCAACCAGTCCACCCAC-3';

(SEQ ID NO: 31)
5'-GTGGGAATCCAAACCCAACCGAGTCCACCCAC-3'.
```

For example, a fragment of the aptamer of SEQ ID NO: 2 is:

```
                                       (SEQ ID NO: 32)
5'-TTGTGTCTGTTCACTCGTCGATACACAG-3';

(SEQ ID NO: 33)
5'-TTGTGTCTGTTCACTCGTCGATACACAGA-3';

(SEQ ID NO: 34)
5'-TTGTGTCTGTTCACTCGTCGATACACAGT-3';

(SEQ ID NO: 35)
5'-TTGTGTCTGTTCACTCGTCGATACACAGC-3';

(SEQ ID NO: 36)
5'-TTGTGTCTGTTCACTCGTCGATACACAGG-3';

(SEQ ID NO: 37)
5'-ATTGTGTCTGTTCACTCGTCGATACACAG-3';

(SEQ ID NO: 38)
5'-CTTGTGTCTGTTCACTCGTCGATACACAG-3';

(SEQ ID NO: 39)
5'-GTTGTGTCTGTTCACTCGTCGATACACAG-3';

(SEQ ID NO: 40)
5'-TTTGTGTCTGTTCACTCGTCGATACACAG-3';

(SEQ ID NO: 41)
5'-AATTGTGTCTGTTCACTCGTCGATACACAG-3';

(SEQ ID NO: 42)
5'-TATTGTGTCTGTTCACTCGTCGATACACAG-3';

(SEQ ID NO: 43)
5'-CATTGTGTCTGTTCACTCGTCGATACACAG-3';

(SEQ ID NO: 44)
5'-GATTGTGTCTGTTCACTCGTCGATACACAG-3';

(SEQ ID NO: 45)
5'-TTGTGTCTGTTCACTCGTCGATACACAGAA-3';

(SEQ ID NO: 46)
5'-TTGTGTCTGTTCACTCGTCGATACACAGAT-3';

(SEQ ID NO: 47)
5'-TTGTGTCTGTTCACTCGTCGATACACAGAC-3';

(SEQ ID NO: 48)
5'-TTGTGTCTGTTCACTCGTCGATACACAGAG-3';

(SEQ ID NO: 49)
5'-TTGTGTCTGTTCACTCGTCGATACAGTA-3';

(SEQ ID NO: 50)
5'-TTGTGTCTGTTCACTCGTCGATACACAGTT-3';

(SEQ ID NO: 51)
5'-TTGTGTCTGTTCACTCGTCGATACACAGTC-3';

(SEQ ID NO: 52)
5'-TTGTGTCTGTTCACTCGTCGATACACAGTG-3';

(SEQ ID NO: 53)
5'-TTGTGTCTGTACACTCGTCGATACACAG-3';

(SEQ ID NO: 54)
5'-TTGTGTCTGTTCACTCCTCGATACACAG-3';

(SEQ ID NO: 55)
5'-TTGTGTCTGTTCAACTCGTCGATACACAG-3';

(SEQ ID NO: 56)
5'-TTGTGTCTGTTCACTCGTCGGATACACAG-3'.
```

For example, a fragment of the aptamer of SEQ ID NO: 57 is:

```
                                       (SEQ ID NO: 59)
5'-TTGTGTCTGTTCACTCGTCGATACACAA-3';

(SEQ ID NO: 60)
5'-TTGTGTCTGTTCACTCGTCGATACACAAA-3';

(SEQ ID NO: 61)
5'-TTGTGTCTGTTCACTCGTCGATACACAAT-3';

(SEQ ID NO: 62)
5'-TTGTGTCTGTTCACTCGTCGATACACAAC-3';

(SEQ ID NO: 63)
5'-TTGTGTCTGTTCACTCGTCGATACACAAG-3';

(SEQ ID NO: 64)
5'-ATTGTGTCTGTTCACTCGTCGATACACAA-3';

(SEQ ID NO: 65)
5'-CTTGTGTCTGTTCACTCGTCGATACACAA-3';

(SEQ ID NO: 66)
5'-GTTGTGTCTGTTCACTCGTCGATACACAA-3';

(SEQ ID NO: 67)
5'-TTTGTGTCTGTTCACTCGTCGATACACAA-3';

(SEQ ID NO: 68)
5'-AATTGTGTCTGTTCACTCGTCGATACACAA-3';

(SEQ ID NO: 69)
5'-TATTGTGTCTGTTCACTCGTCGATACACAA-3';

(SEQ ID NO: 70)
5'-CATTGTGTCTGTTCACTCGTCGATACACAA-3';

(SEQ ID NO: 71)
5'-GATTGTGTCTGTTCACTCGTCGATACACAA-3';

(SEQ ID NO: 72)
5'-TTGTGTCTGTTCACTCGTCGATACACAAAA-3';

(SEQ ID NO: 73)
5'-TTGTGTCTGTTCACTCGTCGATACACAAAT-3';

(SEQ ID NO: 74)
5'-TTGTGTCTGTTCACTCGTCGATACACAAAC-3';

(SEQ ID NO: 75)
5'-TTGTGTCTGTTCACTCGTCGATACACAAAG-3';

(SEQ ID NO: 76)
5'-TTGTGTCTGTTCACTCGTCGATACACAATA-3';

(SEQ ID NO: 77)
5'-TTGTGTCTGTTCACTCGTCGATACACAATT-3';

(SEQ ID NO: 78)
5'-TTGTGTCTGTTCACTCGTCGATACACAATC-3';
```

-continued

```
                                          (SEQ ID NO: 79)
5'-TTGTGTCTGTTCACTCGTCGATACACAATG-3';

(SEQ ID NO: 80)
5'-TTGTGTCTGTACACTCGTCGATACACAA-3';

(SEQ ID NO: 81)
5'-TTGTGTCTGTTCACTCCTCGATACACAA-3';

(SEQ ID NO: 82)
5'-TTGTGTCTGTTCAACTCGTCGATACACAA-3';

(SEQ ID NO: 83)
5'-TTGTGTCTGTTCACTCGTCGGATACACAA-3'.
```

According to another embodiment, a sequence that has at least 60% identity in nucleotides with SEQ ID NO: 1 or SEQ ID NO: 2 or SEQ ID NO: 57 according to the invention, differs in particular from SEQ ID NO: 1 or 2 or 57 by the insertion, suppression or substitution of at least one nucleotide. As understood here, the identity percentage between two sequences is defined as the number of positions for which the bases are identical when the sequences are aligned optimally, divided by the total number of bases of the larger of the two sequences. Two sequences are said to be optimally aligned when the identity percentage is maximal. Moreover, as shall appear clearly to those skilled in the art, it may be necessary to resort to adding gaps so as to obtain an optimal alignment between the two sequences.

The present invention relates to a modified aptamer, i.e. an aptamer according to the invention comprising at least one additional group in addition to the nucleic acid. As such, the nucleic acid according to the invention can be bound to at least one additional group. Preferentially, the aptamer according to the invention is constituted of the nucleic acid according to the invention and of at least one additional group according to the invention.

In one embodiment, the additional group of the invention can as such be a radioisotope, an organic molecule comprising 100 carbon atoms at most, a nanoparticle, a protein, in particular a glycoprotein, a carbohydrate, a lipid, or a polynucleotide. In an embodiment, the additional group of the invention is selected from the group comprising in a non-limiting manner: a detectable marker, a pharmacological compound, and a compound able to modify the pharmacokinetic characteristics of a nucleic acid to which it is bound, such as polyethylene glycol (PEG), a structure 3'-CAP- and/or 5'-CAP-structure and/or a modified nucleotide guanosine (such as 7-methyl-guanosine) in 3'- and/or in 5' of the aptamer.

In one embodiment, the additional group of the invention stabilises the aptamer of the invention by increasing its half-life.

In one embodiment, the aptamer is PEGylated.

In one embodiment, the additional group of the invention is an L and/or D enantiomer of the aptamer of the invention.

The detectable marker of the invention comprises but is not limited to: a fluorophore, for example fluorescein or luciferase; a radioisotope, in particular adapted to scintigraphy, for example 99mTc; a label that can be recognised by an antibody, for example the protein c-Myc; an affinity label, for example biotin; an enzyme, for example horseradish peroxidase.

According to another embodiment, the aptamer according to the invention can be modified, entirely or partially, in particular to make it resistant to a hydrolytic degradation, in particular due to the action of nuclease. Such modifications are well known to those skilled in the art and cover in particular the modifications of the OH function on the carbon in position 2' of the ribose par methylation, or the substitution of this OH function with an amino group or with a halogen, in particular with fluorine, as well as recourse to a phosphorothioate backbone, or to structures of the locked nucleic acid (LNA) or peptide nucleic acid (PNA) type. As such, preferably, the aptamer according to the invention is a RNA of which the riboses of the pyrimidine nucleotides carry one fluorine atom on the carbon in position 2', with the riboses of the purine nucleotides able to be unchanged.

In one embodiment of the invention, the aptamer of the invention can be modified in such a way as to cause to enter via vectorisation the aptamer of the invention into a cell and/or a tissue and/or an organ and/or the target cell compartment. This modification can be made by adding an additional group for the vectorisation.

A purpose of the vectorisation is to preserve the aptamer of the invention, to increase its solubility in case of excessive hydrophobicity, to reduce its toxicity. The vectorisation can also have for objective to spatially, temporally and quantitatively control the distribution of the aptamer of the invention in the organism. For example, the vectors can carry a targeting molecule, which can be in an embodiment the ligand of a receptor, or an antibody against an overexpressed protein in the tissues involved. The vectorisation can also concern a transgene of which the expression shall be targeted by a chimeric protein. In an embodiment the aptamer of the invention can be encapsulated with an imaging agent. The use of vectors that are sensitive to stimuli such as pH or temperature can also make it possible to accelerate the releasing or to provoke it at the desired location.

In one embodiment, a peptide or nucleic sequence or an addressing molecule can be added in order to ensure the vectorisation or the targeting of the aptamer of the invention to STAT5. In another embodiment, a peptide sequence such as the sequence TAT can for example be added in order to favour the entry of the aptamer of the invention into the lymphocytes. In another embodiment of the invention, a chimeric construction comprising a peptide penetrating the cells can be added to an aptamer according to the invention. In another embodiment of the invention, methods of encapsulation such as micelles, polymersomes, liposomes, viruses comprising the aptamer of the invention could be used. These methods of vectorisation and their implementation are well known to those skilled in the art.

The present invention also relates to a composition comprising at least one aptamer according to the present invention.

In one embodiment, the composition of the invention comprises at least SEQ ID NO: 1 or a fragment or variant of SEQ ID NO: 1 such as described hereinabove.

In another embodiment, the composition of the invention comprises at least SEQ ID NO: 2 or a fragment or variant of SEQ ID NO: 2 such as described hereinabove.

In another embodiment, the composition of the invention comprises at least SEQ ID NO: 57 or a fragment or variant of SEQ ID NO: 57 such as described hereinabove.

In another embodiment, the composition of the invention comprises SEQ ID NO: 1 or a fragment or variant of SEQ ID NO: 1 such as described hereinabove and SEQ ID NO: 2 or a fragment or variant of SEQ ID NO: 2 such as described hereinabove.

In another embodiment, the composition of the invention comprises SEQ ID NO: 1 or a fragment or variant of SEQ ID NO: 1 such as described hereinabove and SEQ ID NO: 57 or a fragment or variant of SEQ ID NO: 57 such as described hereinabove.

In another embodiment, the composition of the invention comprises SEQ ID NO: 57 or a fragment or variant of SEQ ID NO: 57 such as described hereinabove and SEQ ID NO: 2 or a fragment or variant of SEQ ID NO: 2 such as described hereinabove.

In another embodiment, the composition of the invention comprises (i) SEQ ID NO: 1 or a fragment or variant of SEQ ID NO: 1 such as described hereinabove, and (ii) SEQ ID NO: 2 or a fragment or variant of SEQ ID NO: 2 such as described hereinabove and (iii) SEQ ID NO: 57 or a fragment or variant of SEQ ID NO: 57 such as described hereinabove.

The present invention also relates to a pharmaceutical composition comprising at least the composition of the invention, in combination with a pharmaceutically acceptable excipient.

The present invention also relates to a medicament comprising at least the composition of the invention.

The present invention also relates to an aptamer of the invention, or a composition, pharmaceutical composition or medicament of the invention to treat, or for its use in the treatment of a disease linked to STAT5, in a subject that needs it.

In one embodiment, a disease linked to STAT5 corresponds to an overexpression of the gene and/or protein expression of STAT5.

In another embodiment, a disease linked to STAT5 corresponds to an overactivation of the biological activity of STAT5.

In another embodiment, a disease linked to STAT5 corresponds to a deregulation of the biological activity of STAT5.

According to a first embodiment, the disease linked to STAT5 is a cancer. Examples of cancers include but are not limited to leukaemia, acute leukaemia, chronic leukaemia, lymphoblastic or lymphatic leukaemia, myeloblastic leukaemia, Acute lymphoblastic leukaemia, Chronic lymphoblastic leukaemia, Acute myeloblastic leukaemia, Chronic lymphatic leukaemia, Chronic myelogenous leukaemia, Juvenile myelomonocytic leukaemia, Galton's T-cell prolymphocytic leukaemia, Mycosis fungoide, with suppressor T lymphocytes, tricholeukaemia, and large lymphocyte leukaemias, prostate cancer, breast cancer, metastatic breast cancer, lung cancer, cancer of the pancreas, intestinal cancer, uterine cancer, colorectal cancer, a preferred cancer is leukaemia.

According to a second embodiment, the disease linked to STAT5 is a cancer linked to an overexpression and/or an overactivation of STAT5 and/or a deregulation of the biological activity of STAT5. Examples of these diseases include but are not limited to: leukaemia, acute leukaemia, anaplastic large cell lymphoma, Sezary syndrome, lymphoblastic or lymphatic leukaemia, myeloblastic leukaemia, Acute lymphoblastic leukaemia, Chronic lymphoblastic leukaemia, Acute myeloblastic leukaemia, Chronic myelogenous leukaemia, Burkitt's leukaemia, Juvenile myelomonocytic leukaemia, Chronic myelomonocytic leukaemia, Galton's T-cell prolymphocytic leukaemia, Mycosis fungoide, tricholeukaemia, and large lymphocyte leukaemias, prostate cancer, breast cancer, metastatic breast cancer; more preferably the disease linked to STAT5 is a leukaemia.

According to a third embodiment, the disease linked to STAT5 is a leukaemia. Examples of leukaemia include but are not limited to: acute leukaemia, chronic leukaemia, lymphoblastic or lymphatic leukaemia, myeloblastic leukaemia, Acute lymphoblastic leukaemia, Chronic lymphoblastic leukaemia, Acute myeloblastic leukaemia, Chronic lymphatic leukaemia, Chronic myelogenous leukaemia, Juvenile myelomonocytic leukaemia, Galton's T-cell prolymphocytic leukaemia, Mycosis fungoide, tricholeukaemia, and large lymphocyte leukaemias.

The acute myeloid leukaemias (or AML) include different stages: AML 0: undifferentiated; AML 1: myeloblastic without differentiation; AML 2: myeloblastic with differentiation; AML 3: promyelocytic; AML 4: myelomonocytic; AML 4Eo: myelomonocytic with eosinophilia; AML 5: monoblastic (without differentiation: M5a, with differentiation: M5b); AML 6: erythroblastic or erythroleukaemia; AML 7: megacaryoblastic. Likewise, acute lymphatic leukaemias (or ALL) include the following stages: ALL 1; ALL 2; ALL 3 or Burkitt's leukaemia; type L3 always corresponding to B proliferations. The L1 and L2 types can correspond to pre-B or pro-pre-B proliferations, with variable degrees of differentiation, or to T proliferations.

In the case where this classification was to change, those skilled in the art would know to which type of disease the new classification would correspond.

In one embodiment, the disease linked to STAT5 does not comprise chronic lymphocytic leukaemia; Tricholeukaemia; Large lymphocyte leukaemias; or Prolymphocytic leukaemias.

According to one embodiment of the invention, the composition, the pharmaceutical composition or the medicament of the invention are adapted for oral administration. In terms of this invention, the term "oral administration" means an administration in the oral cavity, followed by the ingestion of an aptamer according to the invention, which joins the systemic circulation following the intestinal absorption thereof.

According to one embodiment of the invention, the composition, the pharmaceutical composition or the medicament of the invention is in a solid form. Examples of solid formulations adapted for oral administration include, but are not limited to, granules, a powder, a capsule, a tablet, an ointment, a gel, a powder to be dissolved, a paste, a gum to be chewed, a flexible capsule or a soft capsule.

Examples of solid vehicles, diluents or excipients include, but are not limited to glucose, fructose, sucrose, maltose, yellow dextrin, white dextrin, maltodextrin, microcrystalline cellulose, calcium stearate, magnesium stearate, sorbitol, glucose syrup, lactose, citric acid, tartaric acid, malic acid, succinic acid, lactic acid, L-ascorbic acid, alpha-tocopherol, glycerol, propylene glycol, sucroester, glyceryl fatty acid poly esters, sucroglycerides, behenate mono-, di- and triglycerides, carrageenans, gum arabic, casein, gelatine, pectin, agar, nicotinamide, amino acids, calcium salts, pigments.

According to another embodiment of the invention, the composition, the pharmaceutical composition or the medicament of the invention is in liquid form. Examples of liquid formulations adapted oral administration include, but are not limited to, a solution, a suspension, an emulsion (emulsion of oil in water, water in oil, anhydrous, solid or microemulsions), a spray, an inhaler, a vial comprising the composition, the pharmaceutical composition or the medicament of the invention, a powder to dissolve, a beverage or a syrup.

Examples of liquid vehicles include, but are not limited to, distilled water, a saline solution, an aqueous glucose solution, alcohol for example ethanol, propylene glycol, and polyethylene glycol; and oily vehicles such as plant and animal oils, paraffin, or wax.

Examples of antioxidants include but are not limited to tocopherol, butylhydroxytoluene (BHT), butylhydroxyanisol (BHA), natural antioxidants such as vitamin E, rosemary extract, propyl gallate 5.

Examples of antimicrobial preservatives include but are not limited to methylparabene, Propylparaben, potassium sorbate, sodium benzoate, benzoic acid.

Examples of anti-caking agents include but are not limited to silicon dioxide.

Examples of surfactants include but are not limited to anionic, cationic, or non-ionic surfactants such as ascorbyl palmitate, polysorbates, polyethylene glycols.

Examples of pH or buffer stabilisers include but are not limited to sodium citrate-citric acid, sodium phosphate phosphoric acid, sodium acetate-acetic acid.

In another embodiment of the invention, the composition, the pharmaceutical composition or the medicament according to the invention is formulated in the form of controlled-release tablets, using coatings with a polymer base that allow for controlled release thanks to techniques well known to those skilled in the art such as micro-encapsulation or colloidal vehicle systems. Examples of encapsulation agents include, but are not limited to, starch, proteins of animal origin such as, for example, gelatine, proteins of plant origin, casein, pectin, alginate, agar, maltodextrins, lignin sulfonates, cellulose derivatives (ethylcellulose, methylcellulose, hydroxypropylcellulose, hydroxypropylmethylcellulose, carboxymethylcellulose), sugars, sorbitols, gums, etc.

According to one embodiment of the invention, the composition, the pharmaceutical composition or the medicament of the invention are adapted for administration via injection, such as, for example, by intravenous, intrathecal, intradermal, intramuscular or epidural injection.

Examples of formulations adapted for administration via injection include, but are not limited to, an injectable solution and an injectable emulsion (such as, for example, an oil-in-water emulsion, a water-in-oil emulsion, an anhydrous emulsion, a solid emulsion or a microemulsion) comprising the agonists according to the invention.

According to one embodiment of the invention, the composition, the pharmaceutical composition or the medicament of the invention are adapted for topical administration, more preferably for transcutaneous administration. The term "transcutaneous administration" means the administration of a compound on the skin, followed by the absorption thereof into the systemic blood circulation through adjacent skin tissues.

Examples of formulations adapted to topical administration, more preferably transcutaneous include, without being limited thereto, an ointment, a paste, a salve, a gel, a cream or a transdermal patch.

According to one embodiment of the invention, the aptamer according to the invention, or the composition, the pharmaceutical composition or the medicament of the invention is formulated in the form of a unit dosage. Examples of unit doses include, but are not limited to, a tablet, a capsule, a vial or an injectable solution.

The present invention also relates to a unit dose comprising the aptamer according to the invention.

According to one embodiment of the invention, the quantity of the aptamer according to the invention administered to the subject varies from about 1 μg/kg of body mass to about 10 mg/kg of body mass, preferably from about 10 μg/kg to about 5 mg/kg, more preferably from about 50 μg/kg to about 1 mg/kg.

According to another embodiment, those skilled in the art could adapt the administration of the aptamer of the invention according to the type of cancer, the severity of the disease, the age or gender of the subject.

In this invention, the term "subject" designates an animal, more preferably a mammal, more preferentially a human being. According to an embodiment of the invention, the subject is a man. According to another embodiment of the invention, the subject is a woman. According to an embodiment of the invention, the subject is an adult. According to another embodiment of the invention, the subject is a child. According to another embodiment of the invention, the subject is an adolescent. In the present invention, the child subject is 0, 1, 2, 3, 4, 5, 6, 7, 8, 9, 10, 11, 12, 13 years old. In the present invention, the adolescent subject is of the age of 14, 15, 16, 17, 18, 19 years old. In the present invention, the adult subject is at least 20 years old.

In a first embodiment, said subject suffers from a disease linked to STAT5, preferably a cancer, more preferably is diagnosed as suffering from a disease linked to STAT5, preferably a cancer.

In a second embodiment, said subject is at risk of developing a disease linked to STAT5, preferably a cancer.

According to a third embodiment, the subject has non-genetic predispositions for a disease linked to STAT5, preferably for a cancer.

Risk factors that induce cancers include but are not limited to: history of radiotherapy and chemotherapy for another cancer; exposure to radioactivity; exposure in utero to X-rays; exposure to certain chemicals (benzene, aromatic hydrocarbons) or to certain fertilisers; exposure (including in utero at low doses) to certain pesticides; according to a meta study carried out on 31 epidemiological studies conducted between 1950 and 2009, exposure of the pregnant mother during the labour doubles the risk of a leukaemia in the child (40% increase in farmers who seem to be the most exposed). This risk of childhood leukaemia increases the most importantly following exposure to insecticides and herbicides (+2.7 and +3.6 respectively); certain genetic disorders such as trisomy 21; certain diseases such as rickets, certain infections and bone marrow cancer; myeloproliferative haematological diseases: essential polycythaemia or Vaquez's disease, myelofibrosis (fibroblasts in proliferation), aplastic anaemia (many in fact are only leukaemias) while a chronic leukaemia is often transformed into acute leukaemia; exposition to the fumes of certain decorative objects (example: total volatile organic compounds and methanol); or any cause still unknown to date (9 cases out of 10).

According to a fourth embodiment, the subject has genetic predispositions for a disease linked to STAT5, preferably for a cancer, more preferably for a leukaemia.

Examples of diseases diagnosed in a subject increase the risk of developing diseases linked to STAT5. They include in a non-limiting way: myelodysplastic syndromes, Fanconi's disease, trisomy 21, family thrombocytopenia, T-cell Leukaemia Virus-1.

Examples of genetic predispositions for a leukaemia include but are not limited to: mutations in the genes FANCA, FANCB, FANCC, FANCD1 (also known as BRCA2 this gene is involved in family breast cancers), FANCD2, FANCE, FANCF, FANCG, FANCI, FANCJ, FANCL, FANCM and FANCN, p53 deficiency, mutations in the gene GATA2, RUNX1, or the presence of a singular form of the gene PRDM9 in the sexual cells of the parents.

The present invention also relates to a composition, a pharmaceutical composition or a medicament intended to be administered in combination with other anti-cancer agents, (in particular anti-leukemic agents), anti-metastatic agents, anti-folic agents, anti-metabolite agents such as for example antipuric agents, antipyrimidic agents, alkylating agents such as for example nitrogen mustard, nitrosourea, organoplatin, ethylene imine, imidazole amide, intercalating agents such as for example camptothecin derivatives, anthracycline, agents acting on the mitotic spindle such as for example: vinca alkaloid agents, taxoids, tyrosine kinase inhibitors such as for example Dasatinib, Erlotinib, Imatinib, Sorafenib, Sunitinib, anti-angiogenic agents, differentiating agents such as all-trans retinoic acid and arsenic salts, or a mixture thereof.

In one embodiment, the composition, the pharmaceutical composition or the medicament of the invention is intended to be administered before, during, and/or after a chemotherapy treatment.

In another embodiment, the composition, the pharmaceutical composition or the medicament of the invention is intended to be administered before, during, and/or after radiation treatment.

In another embodiment, the composition, the pharmaceutical composition or the medicament of the invention is intended to be administered before, and/or after an allograft.

The present invention also relates to an aptamer of the invention, or a composition, pharmaceutical composition or medicament of the invention intended to be administered in combination with other anti-cancer agents, (in particular anti-leukemic agents), anti-metastatic agents, anti-folic agents, anti-metabolite agents such as for example antipuric agents, antipyrimidic agents, alkylating agents such as for example nitrogen mustard, nitrosourea, organoplatin, ethylene imine, imidazole amide, intercalating agents such as for example camptothecin derivatives, anthracycline, agents acting on the mitotic spindle such as for example: vinca alkaloid agents, taxoids, tyrosine kinase inhibitors such as for example Dasatinib, Erlotinib, Imatinib, Sorafenib, Sunitinib, anti-angiogenic agents, differentiating agents such as all-trans retinoic acid and arsenic salts, or a mixture thereof, to treat, or for its use in the treatment of a disease linked to STAT5, in a subject that needs it.

The present invention also relates to a method for treating a disease linked to STAT5 in a subject, said method comprising the administration to said subject of an effective amount of the aptamer of the invention, or of the composition, pharmaceutical composition or medicament of the invention.

In one embodiment, the method of the invention inhibits and/or stops and/or prevents the overexpression of STAT5 and/or the overactivation of STAT5 and/or the hyperphosphorylation of STAT5 and/or the fixing of STAT5 on the DNA. Those skilled in the art know how to measure by immunochemistry the level of protein phosphorylation.

In another embodiment, the method of the invention inhibits and/or stops and/or prevents the proliferation of cancer cells. Those skilled in the art can measure the proliferation of cells using well-known methods of prior art, for example by counting.

In another embodiment, the method of the invention induces and/or re-established the mechanisms of the apoptosis of cancer cells. Those skilled in the art can measure the effect of a compound on the mechanisms of the apoptosis using tests such as the MTT tests, the LDH tests, the Tunel test, kits that make it possible to specifically measure various markers of apoptosis such as in FIG. 10 of the present invention.

In another embodiment, the method of the invention inhibits the STAT/Jak signalling pathway. Those skilled in the art know how to measure by immunochemistry, ELISA, the modulation of the STAT/Jak signalling pathway.

Another object of the invention is a method for detecting in vitro STAT5 in a biological sample comprising:
  a. contacting at least one aptamer according to the invention with a sample of cells from a subject taken beforehand;
  b. determining of the quantity of said aptamer bound to said sample.

In one embodiment, the method of detecting can make it possible to follow the change in the disease linked to STAT5.

In an embodiment, said method of diagnosing in vitro of a disease linked to STAT5 in a sample of cells comprises:
  a. contacting at least one aptamer according to the invention with a sample of cells from a subject taken beforehand;
  b. determining of the quantity of said aptamer bound to said sample;
  c. comparing said quantity with a reference control;
wherein an increase in the detection of said aptamer linked to the sample corresponds to the revealing of a disease of the invention.

The term biological sample used in this invention that was taken beforehand comprises but is not limited to a sample of blood, serum, plasma, cells from tissues or organs, cerebrospinal fluid, urine, ascite.

In one embodiment, the reference control such as used in this invention corresponds to a biological sample of which the level of expression STAT5 is known to those skilled in the art. This can entail comparing the level of expression STAT5 coming from the biological sample of a subject with the level of expression STAT5 coming from the biological sample of a subject that does not have a disease linked to STAT5 or from a subject having a disease linked to STAT5.

EXAMPLES

Figure 1:
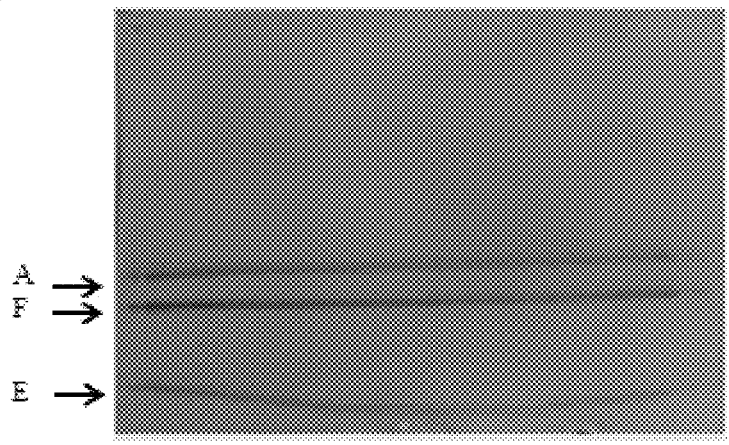
FIG. 1 shows the separation on PAGE-Urea 7M (Gel 15% PAGE-Urea 7M of the sense and antisense strands of aptamers selected and amplified by PCR. The product of the PCR (100 µL+25 µL Urea 5×) is deposited in a single well and the migration in TBE buffer is carried out 55 minutes at 200 V (A) Revelation by measuring the fluorescence. (B) Revelation with methylene blue.
Figure 1:
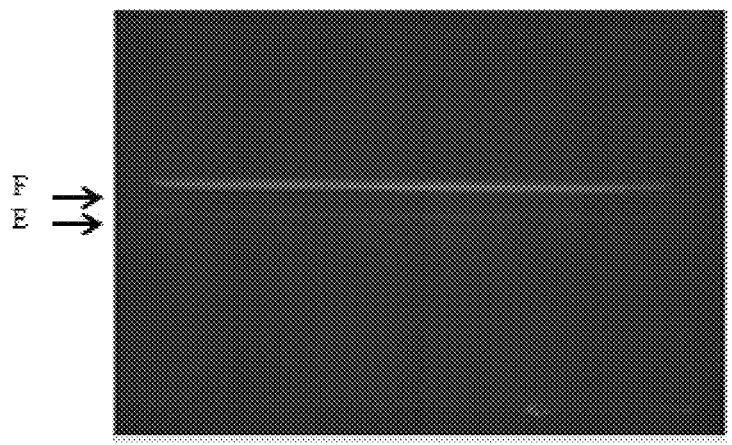

The present invention is further illustrated by the following examples.

Material and Methods

Method for Producing STAT5 Recombinant Proteins:

Digestion

The extraction of the pTAT/HA plasmid is carried out using bacterial pre-cultures of 24 h with the QiaPrep Spin Mini-Prep kit (Qiagen).

The gene stat5B is digested by EcoRI and KpnI in the following conditions: Plasmid pTAT/HA/stat5B 1 µg, KpnI 1 unit, EcoRI 1 unit, NEB-1 1×, BSA 1×, H$_2$O up to 50 µL. The mixture is incubated 1 h at 37° C.

Ligation of the Gene stat5B in the Vector pRSETB

The vector pRSETB is digested by KpnI and EcoRI in the same conditions as the gene stat5B.

pRSET is dephosphorylated by the action of an alkaline phosphatase, Rapid Alkaline Phosphatase (Roche) in the following conditions: plasmid DNA 1 µg (maximum), Rapid Alkaline phosphatase buffer 1×, Rapid Alkaline phosphatase 1 unit, H$_2$O up to 20 µL. The mixture is incubated 10 minutes at 37° C. then 2 minutes at 75° C.

The ligation is carried out in the following conditions: plasmid DNA 1 (maximum), Insert 1 µg (maximum), Ligation buffer 1×, T4 DNA ligase (Roche) 3 units, H$_2$O up to 30 µl. The mixture is incubated at 16° C. for 12 h.

Bacterial Transformation Via the pRSETB/stat5B Construction

The *E. Coli* cells are made competent beforehand, are transformed by the pRSETB/stat5B plasmid construction.

100 ng of DNA are added to 100 µL of competent cells that have just been thawed and are stored on ice. The whole is incubated 20 minutes on ice, then 45 seconds at 42° C. The mixture is then cooled 2 minutes on ice. 900 µL of SOC medium ((1% Tryptone; 1% yeast extract; 10 mM NaCl; 2.5 mM KCl; 10 mM MgCl2; 10 mM MgSO4; 20 mM glucose) preheated to 37° C. are added and the mixture is incubated 1 h 30 at 37° C. under slight agitation. 100 µL are spread in Petri dishes containing the LB-Agar/Ampicilline solid medium (1% Tryptone; 1% yeast extract; 10 mM NaCl; 2% agar; Ampicilline 100 µg/mL). The clones grow at 37° C. during the night. The clones are put into culture and stored at −80° C. in 15% glycerol.

Production, Purification and Renaturation of the STAT5B Recombinant Proteins

10 µL of glycerolated stock of cells transformed by pRSETB/STAT5B are added to 10 mL of LB/ampicillin medium (5 g NaCl, 5 g of yeast extract, 10 g of Tryptone; 100 µg/mL of ampicillin). The cells are cultivated 12 hours at 37° C. under agitation (180 rpm—INFORS HT).

The culture is diluted in such a way that the absorbance at 600 nm is 0.1 then put back at 37° C. under agitation (180 rpm—INFORS HT).

The induction of the protein production is carried out when the culture reaches an absorbance at 600 nm of 0.4 to 0.6. The proteins are then extracted from cells.

The recombinant proteins are purified over Ni-NTA Agarose resin (Qiagen). The STAT5B recombinant proteins are renatured via successive dialyses Measuring the Quantity of Proteins (BCA Test)

A standard range of concentration of Bovin Serum Albumin (BSA) is prepared (0; 25; 50; 75; 100; 150; 200; 300 and 500 µg/mL). The BCA reagent is comprised of a solution A of bicinchoninic acid and of a solution B at 4% copper sulphate (A/B: 50/1). 10 µL of the range and of each sample are deposited in duplicates in a 96-well plate. The BCA reagent is added at a rate of 200 µL/well. The plate is incubated 30 minutes at 37° C., then the absorbance at 560 nm is measured. The intensity of the color is proportional to the mass concentration of the proteins.

SELEX Isolation Method for Aptamers:

The random bank of oligonucleotides, inspired by Stoltenburg et al (2005 Anal Bioanal Chem. 383(1):83-91) was synthesised in the following form (Eurogentec):

5' ATACCAGCTTATTCAATT N60 AGATAGTAAGTG-CAATCT 3' where N is randomly A, T, G or C (SEQ ID NO: 84).

Capture and Elution

Purified STAT5B proteins are captured on Dynabeads® His-Tag Isolation & Pulldown (Dynal) beads by incubation (1 hour at ambient temperature) of 2 mg of beads with 150 to 200 µg of STAT5B proteins. The oligonucleotide bank is added at a rate of 3 nmol (round 1) or 200 pmol (round 2 at n). The binding/washing buffer is added up to 700 µL to the beads that are incubated overnight under agitation at 4° C.

The elution of aptamers fixed to STAT5B is carried out by adding 200 µL of elution buffer (10 mM EDTA; 40 mM Tris-HCl; 3.5 mM Urea; 0.02% Tween-20) and by incubating 7 minutes at 80° C. The elution is repeated 2 times.

Amplification and Separation of the Aptamers

The aptamers are amplified by PCR by using the following primers, one (sense) fluorescent, the other (antisense) charged:

```
Sense
                                    (SEQ ID NO: 9)
5'-Fluo-ATACCAGCTTATTCAATT-3';

Anti-sense
                                    (SEQ ID NO: 10)
5'-Poly-dA20-AGATTGCACTTACTATCT-3'.
```

The PCR mixture is as follows: Aptamer (recovered in entirety, i.e. about 3 pmol); polymerase DNA (Vent polymerase—New England Biolabs) 2 units; Sense primers 10 µM; Anti-sense primers 10 µM; Buffer of PCR 1×; dNTP 25 mM; H$_2$O up to 50 µl.

The temperature cycles are carried out in a Biorad C1000™ Thermal Cycler according to the following programme (Table 1):

TABLE 1

PCR cycles for the amplification of the selected aptamers.

|  | Cycles | Time | Temperature |
|---|---|---|---|
| Initial denaturation | 1 | 5 min | 94° C. |
| Denaturation |  | 1 min | 94° C. |
| Hybridation | 30 | 1 min | 47° C. |
| Elongation |  | 1 min | 72° C. |
| End of elongation | 1 | 1 min | 72° C. |
|  |  | ∞ |  |
| End of reaction | 1 |  | 4° C. |

The sense and antisense strands are separated by PAGE-Urea 7 M electrophoresis after purification on QIAquick PCR Purification column (Qiagen). The results are revealed with UV.

The sense strands are then purified using the band detected with UV. The band is cut and plunged into the diffusion buffer of the NucleoSpin Gel Kit (Macherey Nagel), at a rate of 200 µL for 100 ng of gel. The piece of gel is crushed and incubated overnight at 37° C., then centrifuged 5 minutes at 13,000 g. 2 volumes of NTC buffer (supplied by the kit) are added to the supernatant. The aptamers are purified with the Clean-up kit (Macherey-Nagel), by repeating the step of elution 5 times.

Sequencing of the Selected Aptamers

The analysis of the selected aptamers is carried out by cloning sequences retained in an adapted system of expression. The cloning is carried out by the intermediary of the expression vector pGEMT®. The sequencing is carried out using standard primers T7.

Revealing of the Aptamer-STAT5 Interaction:
Extraction of the Activated STAT5 Cell Proteins.

Two activated cell sources of STAT5 were used:

the Ba/F3 pro-lymphocytic murine line transformed by the oncogenic form of STAT5B, called STAT5B 1*6;

the KU-812 myeloid human line, established using a patient afflicted with chronic myelogenous leukaemia (with chromosome Ph).

The following experiments are carried out cold (on ice and centrifugations at 4° C.).

10 million cells are centrifuged 2 minutes at 260 g. The cell pellet is washed via cold PBS (with 5 mL, then with 1 mL) then centrifuged in the same way. The cellules are placed in 50 µL of buffer EC (Hepes 20 mM pH7.9; KCl 10 mM; EDTA 1 mM; NP40—Tergitol® 0.2%; Glycerol 10% to which are added extemporaneously: PhenylMethylSulfonyl Fluoride 2 mM; Dithiothreitol 1 mM; Sodium orthovanadate 1 mM; Complete EDTA Free—Roche), incubated 5 minutes in the ice, then centrifuged 2 minutes at 12,000 g. The supernatant contains the STAT5 proteins of the cytoplasm.

The pellet is then taken up by 50 µL of buffer EN (Hepes 20 mM pH7.9; KCl 10 mM; EDTA 1 mM; NaCl 400 mM; Glycerol 20% to which are added extemporaneously: PhenylMethylSulfonyl Fluoride 2 mM; Dithiothreitol 1 mM; Sodium orthovanadate 1 mM; Complete EDTA Free—Roche), incubated 30 minutes in the ice by agitating the tube from time to time. The mixture is then centrifuged 2 minutes at 16,100 g. The supernatant contains the nuclear STAT5 proteins.

Pull Down 200 pmol of biotinylated aptamers are incubated with 200 µg of proteins of cytoplasmic and nuclear extracts for 2 h over ice in the binding/washing buffer (5x: Tris pH 7.5 50 mM; NaCl 50 mM; EDTA 5 mM; PMSF 2.5 mM; Glycerol 25%; NP40—Tergitol® 0.5%). The mixture is then put into contact with 100 µL of streptavidin beads (Dynal) for 30 minutes under agitation at 4° C. The whole is washed 3 times with the washing buffer. The proteins are then eluted by adding 40 µL of elution buffer (Tris 0.5 M 250 mM pH 6.8; Glycerol 25%, SDS 8%, β-mercaptoethanol 20%; $H_2O$ up to 10 mL) and by heating 5 minutes at 90° C.

Electrophoresis and Western Blot

The proteins are analysed by Western Blot after electrophoretic migration on SDS-PAGE gel.

Activated STAT5 proteins are detected by using 2 antibodies (at the concentrations indicated by the supplier): Antibody anti-STAT5 (C-17 Santa Cruz) produced in rabbits; Antibody anti-PhosphoSTAT5 (Y694) produced in rabbits (Cell Signalling).

The specific recognition of these antibodies is then revealed by a secondary antibody (anti-rabbit IgG) marked with peroxidase (Sigma-Aldrich) diluted to 1/5000.

Measuring the Effect of Aptamers on the Cell Lines

The leukemic cell lines are maintained in culture in a RPMI medium, 10% SVF, 1% glutamine, 1% penicillin/streptomycin by incubation at 37° C. in a 5% $CO_2$ wet atmosphere. The transfection of the aptamers is done on 500,000 cells. 6 µg of biotinylated aptamers and 12 of JetPEI (—Polyplus Transfection™) are respectively diluted in 100 µl of NaCl 150 mM. The 2 solutions are mixed and poured on the cells to be treated. The cells are incubated 24 h.

In order to estimate cell viability, the living cells are counted on cell rests of Malassez according to the exclusion test with Trypan Blue.

Measuring the Effect of Aptamers on the Gene Expression

The effect of aptamers on the expression of a complete set of genes was studied on the leukemic cell lines transfected beforehand. The proteins are extracted and analysed by Western Blot with the Human Apoptosis Antibody Array Kit (R&D Systems).

Study of Apoptosis

The TUNEL technique (Terminal deoxynucleotidyl transferase dUTP nick end labelling) is based on the presence in the apoptotic cells of fragments of double-strand DNA with a low molecular weight (mono- or oligonucleosomes) but also single-strand fragments with a high molecular weight. These are the result of the fragmentation of the DNA during the apoptotic process. The principle of the TUNEL technique consists in labelling the ends of these fragments by using the terminal deoxynucleotidyl transferase enzyme that catalyses the adding of the nucleotides marked with fluorescein at the free 3'OH ends.

Example 1: Engineering of STAT5 Protein

The STAT5B murine protein (SEQ ID NO: 8) is generated using a vector pTAT-HA/statB5 vector that was sub-cloned by steps of digestion, ligation, bacterial transformation. Given that prior art has shown a better production of the STAT5B recombinant protein in relation to the STAT5A murine recombinant protein (SEQ ID NO: 7), it was decided to produce STAT5B in order to produce specific aptamers of STAT5. After sequencing, the vector constructions were introduced into a prokaryotic expression system with the purpose of producing the recombinant protein. As with most recombinant protein, STAT5B proteins tend to aggregate and form inclusion bodies in the cytoplasm. The proteins were therefore extracted using these inclusion bodies thanks to denaturing buffers. The proteins are then purified over Ni-NTA resin thanks to the 6-His label merged with the proteins produced. This step is followed by a renaturing step such as described in the equipment and method.

The production/purification balance of the STAT5B recombinant protein is carried out over SDS-PAGE 10% gel. The identification of the band corresponding to Stat5b is validated by a Western Blot. STAT5B protein was indeed extracted and purified. Its degree of purity is sufficient to be used as a target for the SELEX procedure.

The saturation of the beads is optimised. The beads are saturated when a measurable quantity (>25 µg/mL, sensitivity limit of the BCA test) is present in the non-retained fraction.

Example 2: Isolation, Characterisation of STAT5 Aptamers

In order to select specific inhibitors of STAT5B recombinant protein produced hereinabove the strategy implemented was based on the selection of aptamers. The aptamers are synthetic oligonucleotides of DNA or of RNA able to be organised into complex three-dimensional structures. The selection of aptamers reverts therefore to identifying using a bank of nucleic acids the most complementary structures of the target, in other words those generating the most stable interactions.

Aptamers are also characterised by their properties. These are molecules of small size composed of nucleic acids which make them poorly immunogenic. They have a high affinity and remarkable specificity for their target and selectivity. Aptamers can be generated against targets of a very diverse nature ranging from small organic molecules to intact cells, including peptides and other proteins.

The aptamers are isolated in vitro by an iterative selection method called the SELEX method. The SELEX method is initiated using a bank of nucleic acids of which the flanking sequences are known. The banks that are conventionally used contain between $10^{13}$ and $10^{15}$ different sequences. This method makes it possible to select structured ligands with a high affinity and specificity for the protein studied.

This technique consists in contacting a wide randomised band of oligonucleotides with the STAT5B recombinant protein produced hereinabove—isolated—purified and refolded. After incubation the oligonucleotides that have not fixed the target protein are removed via washing while the additional DNA sequences are eluted and amplified by PCR. This step makes it possible to generate a new pool of double-strand DNA. A step of purification on PAGE is required in order to separate the additional strands (of which one of the sequences is homologous to the aptamers and the other is complementary) and as such constitute a new sequence-enriched bank that has a complete affinity that is more or less high for the STAT protein.

The second cycle of SELEX consists in incubating this new DNA-enriched bank with the target protein in order to progressively eliminate the less and less refined sequences.

The SELEX method is therefore based on the repetition of the washing/elution/amplification and purification steps.

In a first step it was therefore necessary to verify the diversity of the DNA bank in order to ensure heterogeneity of the mixture. To do this, the bank was cloned in the pGEMT expression system and the plasmid construction introduced into the competent E. Coli bacteria. The various clones obtained were studied via PCR on colonies and the PCR products were sent for sequencing. The results concerning the 20 sequenced clones make it possible to underline the absence of sequential redundancy and to verify that the oligonucleotides from the initial bank are compliant with the request made of the service provider (Eurogentec). After several cycles, and thanks to the selection pressure only one or a few DNA sequences are retained. Once selected the oligonucleotides are sequenced and studied in order to determine their inhibiting power to the STAT5 transcription factors.

After putting the bank and the STAT5B (SEQ ID NO: 8) protein into contact, washings and elution, the selected aptamers are amplified via PCR. The result of the PCR is deposited on PAGE-Urea 7M gel in order to be characterised (FIG. 1).

The sense strand is made fluorescent via PCR amplification using a modified primer in 5' by a fluorescent group (FIG. 1A, band (A)). The band (F) revealed in fluorescence (FIG. 1A) corresponds to the revelation of excessive fluorescent primers. The discrimination between the sense and antisense strands is carried out thanks to the use of a charged amplification primer with 5' by polyadenylation and pegylation. In FIG. 1B, migration gel coloured with methylene blue, the band corresponding to the charged strand (A), the sense band (F) and the excessive primer band (E) can as such be seen.

Figure 2:
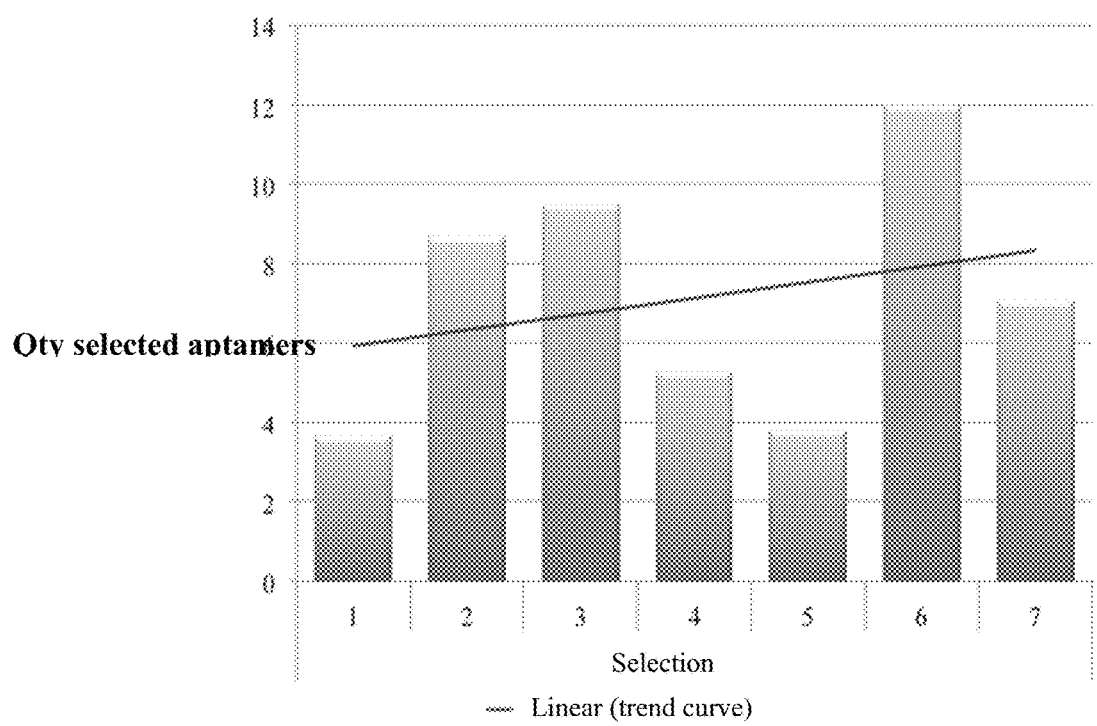
FIG. 2 shows an apparently very spread change in the quantity of the aptamer recovered, but the trend curve indicates that there is an enrichment by a factor of 1.33.

The quantity of aptamers recovered after cutting the band and purification at each round of selection is estimated by measuring the absorbance at 260 nm. The change in this quantity shows the enrichment of the bank with specific aptamers of the target, enrichments which is materialised by the trend curve (FIG. 2). FIG. 2 shows an apparently highly dispersed change, but the trend curve indicates that there is an enrichment by a factor of 1.33. The aptamers are cloned then sequenced.

The following sequences of aptamers were selected:

```
Apta1:
                                        (SEQ ID NO: 3)
5'ATACCAGCTTATTCAATTTATCCGCAACCCACCTAGCGCCCTACCTCGT
GGGAATCCAAACCCAACCAGTCCACCCACAGATAGTAAGTGCAATCT-3;

Apta2:
                                        (SEQ ID NO: 4)
5'ATACCAGCTTATTCAATTGTGTCTGTTCACTCGTCGATACACAGCATAC
TCAACCCAGGCCCCTGACTGCTAATCCCCAGATAGTAAGTGCAATCT-3';

Apta3:
                                        (SEQ ID NO: 58)
5'ATACCAGCTTATTCAATTGTGTCTGTTCACTCGTCGATACACAACATAC
TCAACCCAGGCCCCTGACTGCTAATCCCCAGATAGTAAGTGCAATCT-3'.
```

Figure 3:
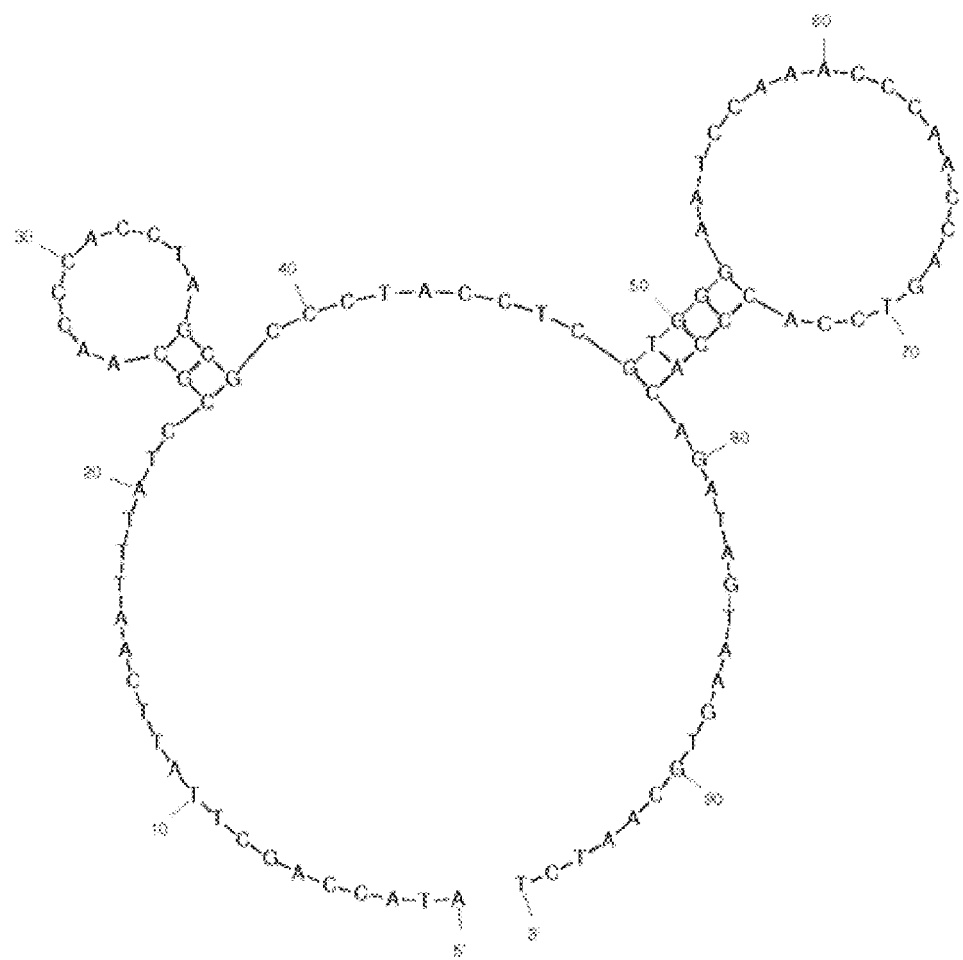
FIG. 3 shows the structure of Apta 1 according to the mfold software.
Figure 4:
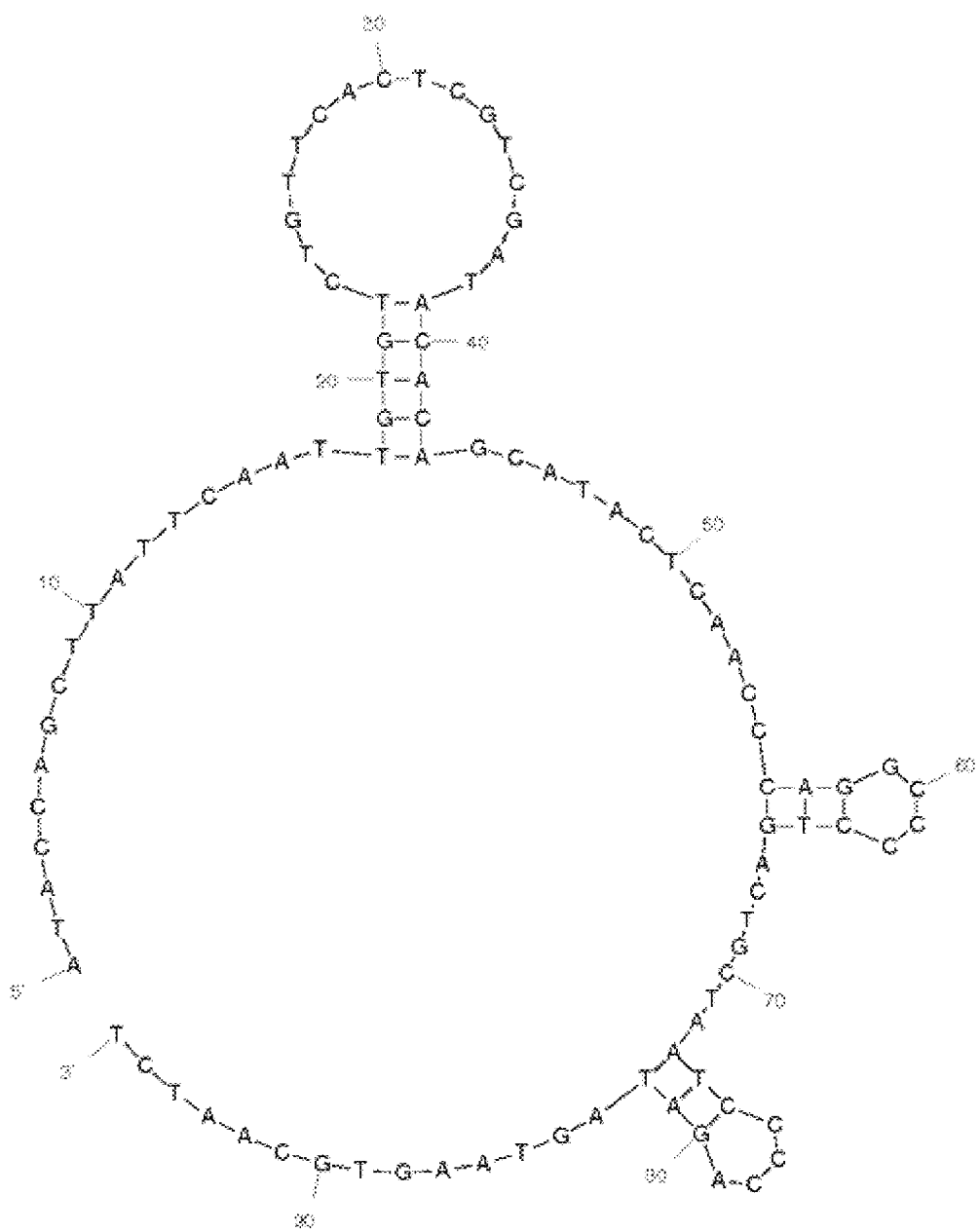
FIG. 4 shows the structure of Apta 2 according to the mfold software.
Figure 5:
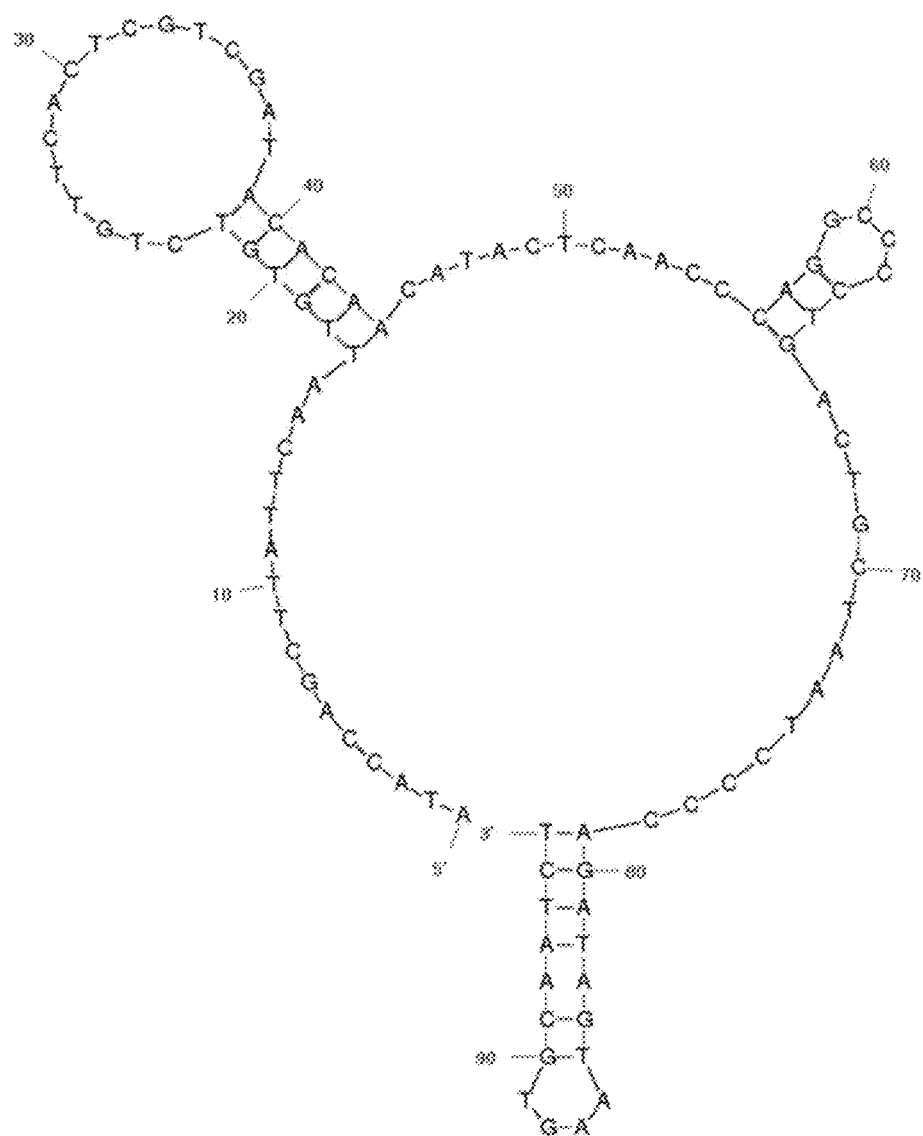
FIG. 5 shows the structure of Apta 3 according to the mfold software.

The modelling of these molecules by the mfold software gives the structure shown (FIG. 3 for Apta 1, FIG. 4 for Apta 2 and FIG. 5 for Apta 3).

The secondary structure of the selected aptamers is carried out using the mfold software available for example on the website of the Michael Zuker laboratory: http://bioinfo.math.rpi.edu/~zukerm or at the following address: http://mfold.rna.albany.edunq=mfold/download-mfold. The algorithm used by this software is also based on the research described in Mathews D H et al (1999 J Mol Biol 288:911-940). The structure of Apta 1 is shown in FIG. 3. The structure of Apta 2 is shown in FIG. 4. The structure of Apta 3 is shown in FIG. 5.

Figure 6:
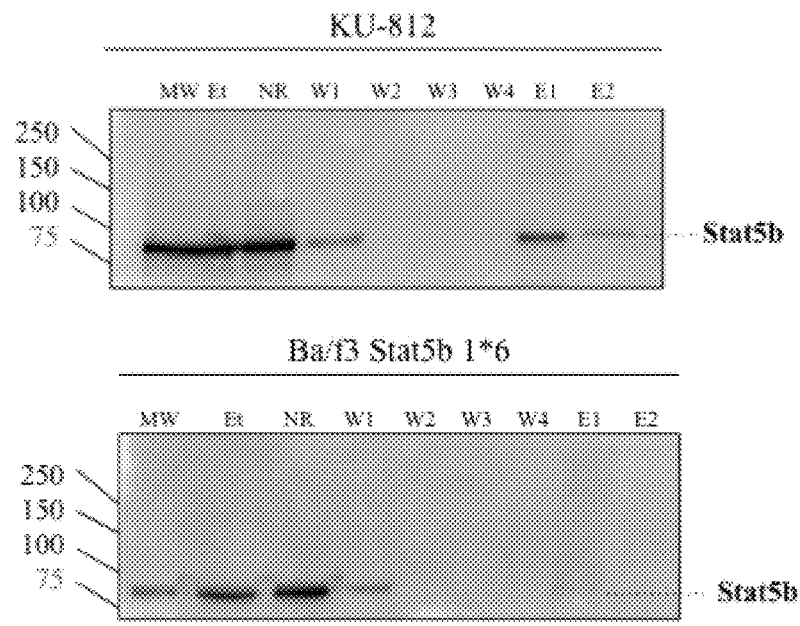
FIG. 6 shows the revealing of the evidence of the interaction between STAT5 and Apta1. The results of the pool down of the Western Blot are shown. MW: Size marker (Dual colour—BIORAD). TP: Total protein extract. NR: Fraction not retained. W1, W2, W3, W4: Successive washing fractions. E1, E2: Successive elution fractions.

The activity of the aptamer Apta1 is tested by Western Blot on the cellular STAT5 (coming from the cytoplasm and the nucleus). The validation of the complementarity of the oligonucleotides selected for the native STAT5B transcription factors is carried out by a pull down experiment in the KU-812 cells and the Ba/f3 STAT5B 1*6 cells (FIG. 6). This experiment shows indeed that Apta1 recognises the cellular STAT5 protein, although it was selected against the recombinant STAT5B protein.

Example 3: Effects of Apta1 on the Cell Lines

Figure 7:
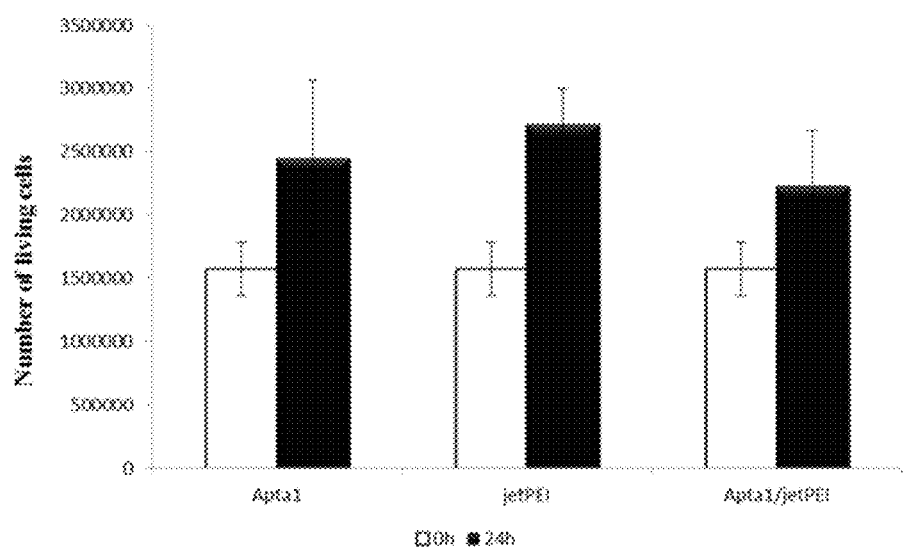
FIG. 7 shows the growth of the KU-812 cells in the absence (JetPEI) or in the presence (Aptamer1/JetPEI) of Apta1. Measurement of the number of cells at t=0 (white), t=24 h (black). Average obtained over 5 experiments.

The growth of KU-812 cells transfected by Apta1 is shown in FIG. 7.

Figure 8:
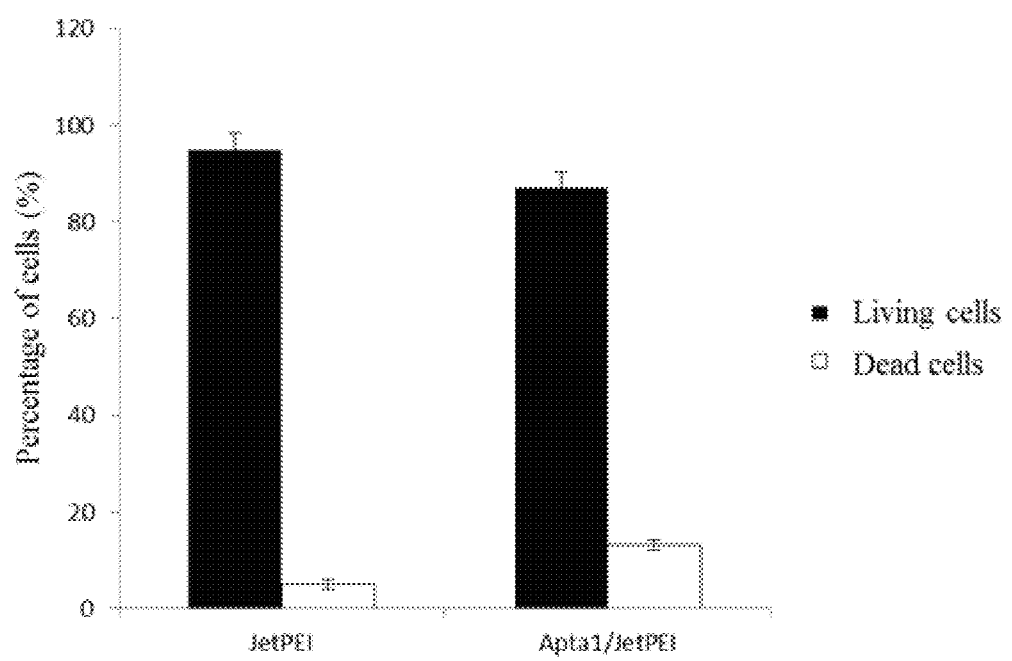
FIG. 8 shows the revealing of the cellular mortality of the KU-812 cells in the absence (JetPEI) or in the presence (Aptamer1/JetPEI) of Apta1, at a rate of 6 µg of DNA/500,000 cells. The cells are coloured with Trypan blue after 24 h of culture and counted on cell rests of Malassez.

The measurement of the growth shows a drop in the number of cells in the presence of Apta1 transfected using JetPEI. Considering that the strands of DNA are degraded very rapidly (a few hours) by cellular nucleases, in particular nuclear, this drop, although slight, indicates the possibility that Apta1 negatively regulates the leukaemogenic activity of STAT5. This hypothesis is all the more so valid in that the effect measured is systematically observed during experiments conducted independently (different unthawings, different experimenters, blind counts). In addition Apta1 has an effect on cellular mortality (FIG. 8).

Figure 9:
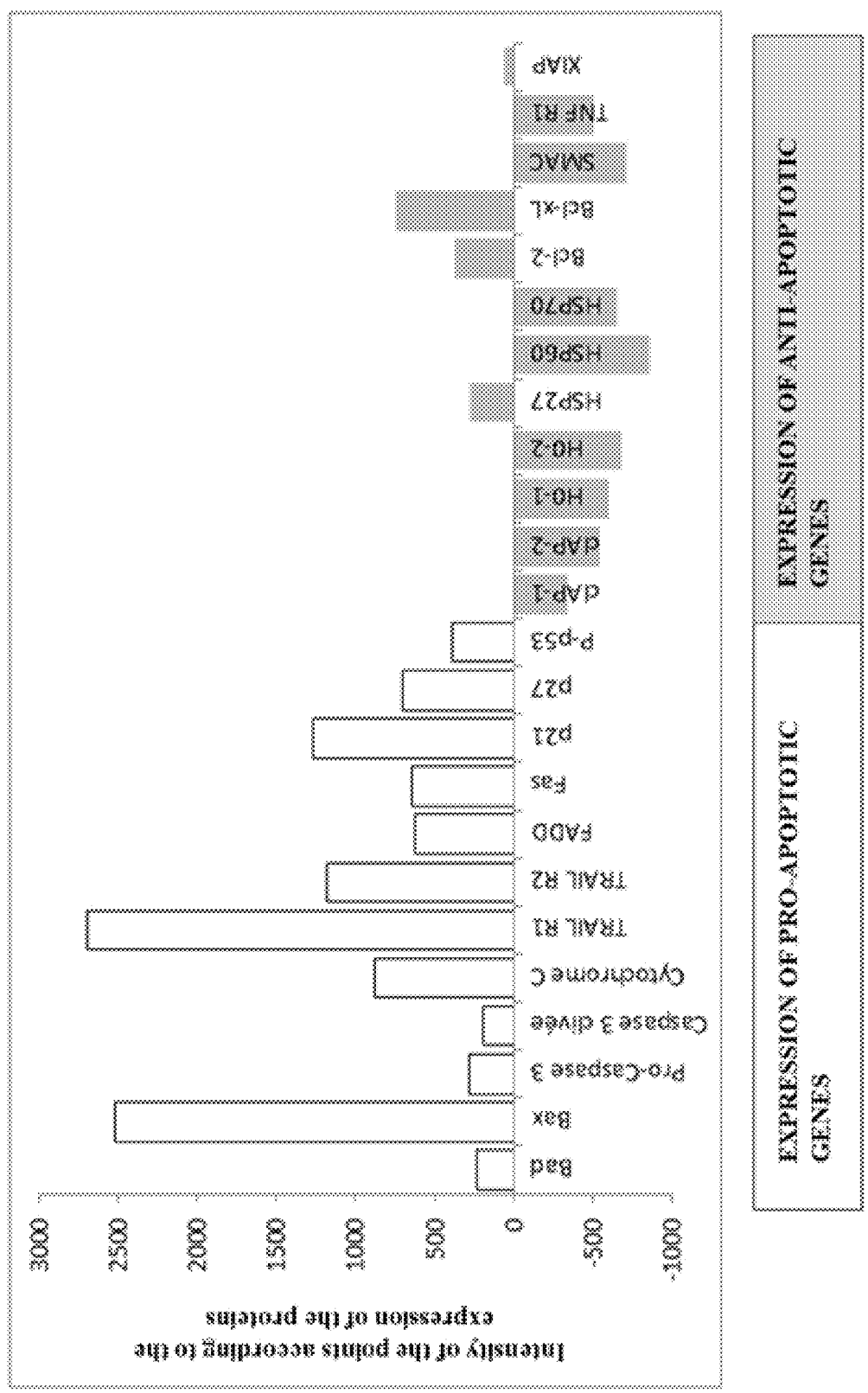
FIG. 9 shows the revealing of the membranes of the Human Apoptosis Antibody Array Kit (R&D Systems). The analysis is carried out using the Image Studio application that measures the intensity of the spots. The intensity of the signal depends on the expression of the target protein in the protein extract. The histograms correspond to the difference in the expression between untreated cells and cells transfected with Apta1/JetPeI for 48 h (300,000 cell/ml).

The effect on the genes involved in the apoptosis is then measured (FIG. 9). According to these measurements, Apta1 significantly increases the activity of the genes that promote apoptosis and also reduce the expression of anti-apoptotic genes of the leukaemia cells.

To resume, Apta1 recognises the recombinant STAT5B protein, STAT5 protein extracted from the cells, decreases cell growth of the leukaemia cells and regulates the expression of the genes involved in the apoptosis.

Example 4: Effects of Apta2 on the Growth of Cell Lines

Figure 10:
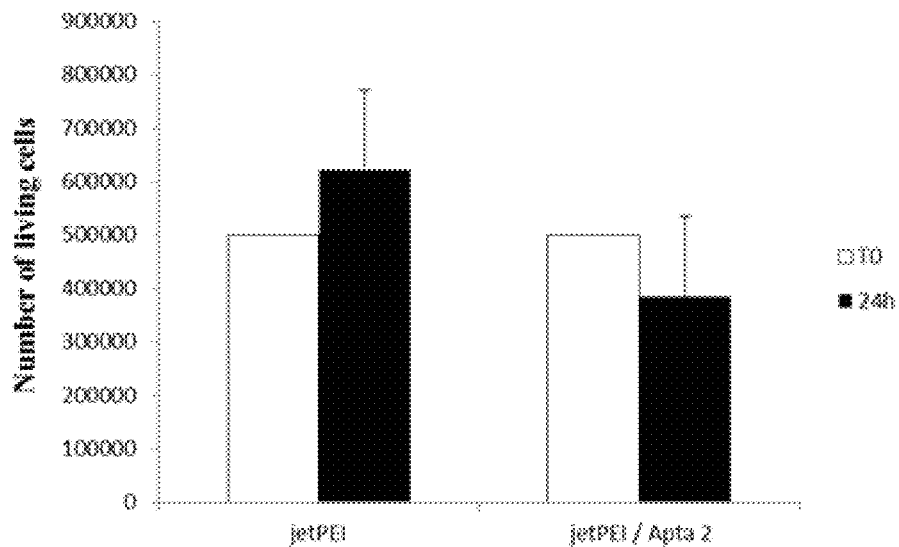
FIG. 10 shows the growth of the KU-812 cells. JetPEI: Cells transfected by JetPEI, JetPEI/Apta2: Cells treated by JetPEI/Apta2. Apta2. Measurement of the number of cells at t=0 (white), t=24 h (black). Average obtained over 2 experiments.

The KU-812 cells were transfected with Apta2. The growth of the KU-812 cells transfected by Apta2 is shown in FIG. 10. Apta2 reduces the growth of KU-812 cells.

Figure 11:
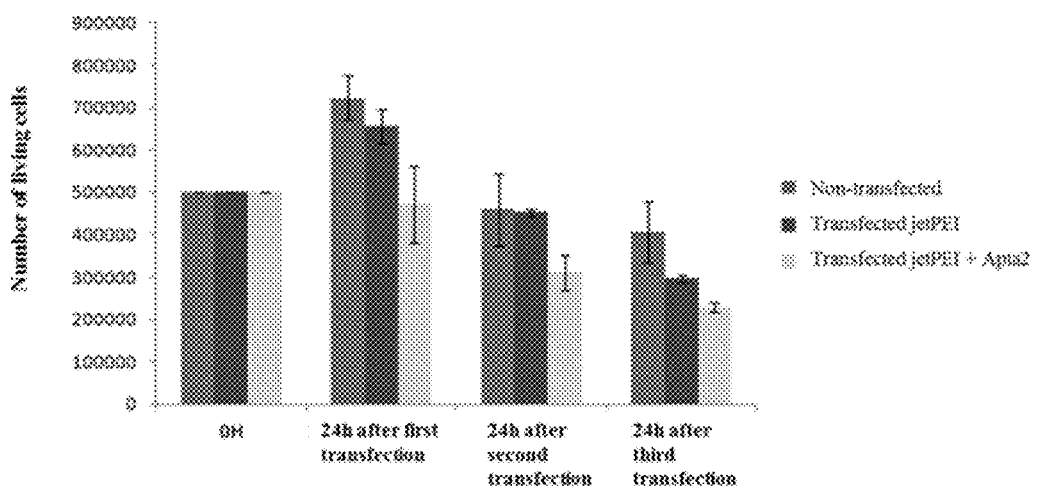
FIG. 11 shows the growth of the transfected KU-812 cells every 24 h with 6 µg of Apta2.

Considering that the effect of Apta2 can only be transient in light of the half-life of a single-strand DNA strand in a cell (i.e. 1 to 3 h), we explored the cumulative effect of Apta2 during successive transfections, carried out every 24 h (FIG. 11). After 24 h, the cells are counted then transfected again, in the same conditions. This method is repeated three times.

It is observed that the cells transfected with Apta2 systematically have a growth less than that of cells that are not transfected or treated with JetPEI alone, which confirms the effect observed hereinabove. On the other hand, the cells suffer after 48 h ($2^{nd}$ transfection), they do not even grow in the control well (without transfection).

Example 5: Effects of Apta2 on Cell Line Viability

Figure 12:
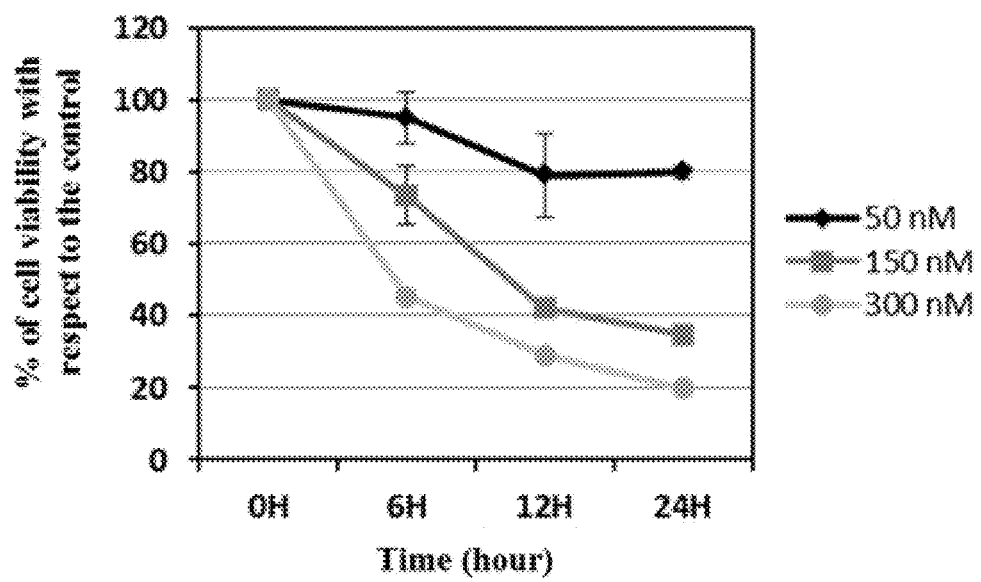
FIG. 12 shows the cell viability of the KU-812 cells transfected by different concentrations of Apta2: 50 nM; 150 nM; 300 nM as a function of time (6 h; 12 h; 24 h).

The KU812 cells were transfected by different concentrations of Apta2: 50 nM, 150 nM and 300 nM in order to test the dose-dependency (FIG. 12). Cell viability was then studied as a function of time. For this, a cell count was carried out, for each of these concentrations after 6 h, 12 h and 24 h of transfection.

The results show a significant effect of apta2 as a function of time and of the dose of aptamer. A statistically significant decrease in the number of living cells after only 6 hours of transfection by 150 nM of Apta2 is observed. The calculation of the percentage of the living cells in relation to the control condition show that only 20% of the cells remain alive after 24 h of transfection by 9 µg (300 nM) of Apta2.

Example 6: Effects of Apta2 on the Apoptosis of the Cell Lines

Figure 13:
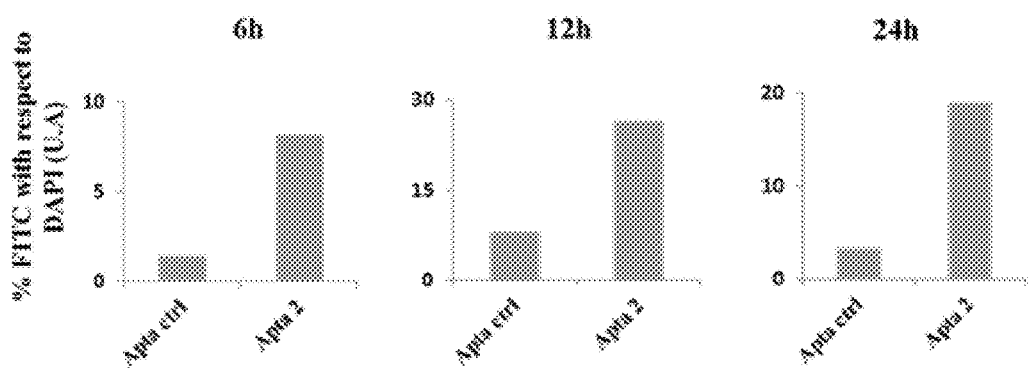
FIG. 13 shows the apoptotic effect of 150 nM of Apta2 transfected in the KU-812 cells.

The observation of the fragmentation of the DNA after transfection was carried out by marking the nuclei with DAPI then by marking fragments on free 3' OH ends with dUTP coupled with fluorescein. The analyse via TUNEL was carried out on the cells that were treated by 150 nM of apta2 and of apta ctrl (sequence Apta2 degenerated) after 6 h, 12 h and 24 h of transfection ((FIG. 13).

The results of the TUNEL in the presence of Apta2 show an increase in the intensity of the fluorescence due to the FITC in the case where the cells are transfected by Apta2. This fluorescence becomes stronger over time indicating an increase in the number of dead cells and as such confirming the results of the study of cell viability. The intensity of the FITC was quantified using the Image Studio Lite software.

The invention claimed is:

1. A DNA aptamer binding specifically to STAT5, preferably to STAT5B, said DNA aptamer being characterized in that it comprises the sequence SEQ ID NO: 1, SEQ ID NO: 2 or SEQ ID NO: 57, or a fragment thereof, or a variant having at least 90% of sequence identity with SEQ ID NO: 1, SEQ ID NO: 2 or SEQ ID NO: 57.

2. The DNA aptamer binding specifically to STAT5 according to claim 1, further comprising an additional stabilization group and/or an additional group for vectorization.

3. The DNA aptamer according to claim 1, in combination with another active agent selected from anti-cancer agents, anti-angiogenic agents, anti-metastatic agents, anti-leukemic agents, anti-folic agents, anti-metabolite agents, alkylating agents, intercalating agents, agents acting on the mitotic spindle, tyrosine kinase inhibitors, differentiating agents, or a mixture thereof, for its use in the treatment of cancers, preferably leukaemia.

4. A method for treating cancer comprising administering to a subject in need thereof an effective amount of a DNA aptamer binding specifically to STAT5, preferably to STAT5B, said DNA aptamer being characterized in that it comprises the sequence SEQ ID NO: 1, SEQ ID NO: 2 or SEQ ID NO: 57, or a fragment thereof, or a variant having at least 90% of sequence identity with SEQ ID NO: 1, SEQ ID NO: 2 or SEQ ID NO: 57, thereby treating cancer in the subject in need thereof.

5. The method according to claim 4, wherein said cancer is leukemia.

6. The method according to claim 4, wherein said DNA aptamer is administered in combination with another active agent selected from anti-cancer agents, anti-angiogenic agents, anti-metastatic agents, anti-leukemic agents, anti-folic agents, anti-metabolite agents, alkylating agents, intercalating agents, agents acting on the mitotic spindle, tyrosine kinase inhibitors, differentiating agents, or a mixture thereof.

7. A method for detecting STAT5 in a biological sample comprising:
   a. contacting a DNA aptamer binding specifically to STAT5, preferably to STAT5B, said DNA aptamer being characterized in that it comprises the sequence SEQ ID NO: 1, SEQ ID NO: 2 or SEQ ID NO: 57, or a fragment thereof, or a variant having at least 90% of sequence identity with SEQ ID NO: 1, SEQ ID NO: 2 or SEQ ID NO: 57 with said sample taken beforehand from a subject,
   b. determining the quantity of said DNA aptamer bound to said sample.

* * * * *